United States Patent
Brown et al.

(10) Patent No.: US 7,152,611 B2
(45) Date of Patent: Dec. 26, 2006

(54) COATED MULTIFILAMENT DENTAL DEVICES OVERCOATED WITH IMBEDDED PARTICULATE

(75) Inventors: Dale G. Brown, Wharton, TX (US); Michael R. Schweigert, Missouri City, TX (US); Ira D. Hill, Locust, NJ (US)

(73) Assignee: International Tape Partners, LLC, Stafford, TX (US)

( * ) Notice: Subject to any disclaimer, the term of this patent is extended or adjusted under 35 U.S.C. 154(b) by 85 days.

(21) Appl. No.: 10/331,795

(22) Filed: Dec. 30, 2002

(65) Prior Publication Data

US 2004/0123877 A1    Jul. 1, 2004

(51) Int. Cl.
*A61C 15/00* (2006.01)

(52) U.S. Cl. .................................................. 132/321

(58) Field of Classification Search ............... 132/321; 424/49–50, 401
See application file for complete search history.

(56) References Cited

U.S. PATENT DOCUMENTS

| | | |
|---|---|---|
| 1,069,874 A | 8/1913 | Hanscom |
| 1,138,479 A | 5/1915 | Hough |
| 1,149,376 A | 8/1915 | Leonard et al. |
| 1,285,988 A | 11/1918 | Gudebrod |
| 1,839,483 A | 1/1932 | Humphrey |
| 1,839,486 A | 1/1932 | Lawton |
| 1,943,856 A | 1/1934 | Cross |
| 1,989,895 A | 2/1935 | Gilder |
| 2,224,489 A | 12/1940 | Rozenbroek |
| 2,381,142 A | 8/1945 | Stonehill |
| 2,464,755 A | 3/1949 | Taub |
| 2,542,518 A | 2/1951 | Henschel |
| 2,554,464 A | 5/1951 | Kraus |
| 2,640,001 A | 5/1953 | Clayton |
| 2,640,002 A | 5/1953 | Clayton |
| 2,667,443 A | 1/1954 | Ashton |
| 2,689,808 A | 9/1954 | Clayton |
| 2,700,636 A | 1/1955 | Ashton |
| 2,748,781 A | 6/1956 | Collat |
| 3,093,501 A | 6/1963 | Clayton |
| 3,330,732 A | 7/1967 | Muhler |
| 3,491,776 A | 1/1970 | Fleming |
| 3,699,979 A | 10/1972 | Muhler et al. ............... 132/89 |
| 3,744,499 A | 7/1973 | Wells ...................... 132/92 A |
| 3,771,536 A | 11/1973 | Dragan ....................... 132/89 |
| 3,800,812 A | 4/1974 | Jaffe ........................... 132/89 |
| 3,830,246 A | 8/1974 | Gillings ....................... 132/89 |
| 3,837,351 A | 9/1974 | Thornton .................... 132/89 |
| 3,838,702 A | 10/1974 | Standish et al. ............ 132/89 |
| 3,848,363 A | 11/1974 | Lovness et al. ................. 51/7 |
| 3,892,908 A | 7/1975 | Lovness ..................... 428/329 |
| 3,897,795 A | 8/1975 | Engel .......................... 132/89 |
| 3,897,796 A | 8/1975 | Erickson ..................... 132/89 |
| 3,943,949 A | 3/1976 | Ashton et al. ............... 132/89 |
| 4,024,295 A | 5/1977 | Chase et al. ................ 422/47 |

(Continued)

FOREIGN PATENT DOCUMENTS

EP    0 887 050 A2    12/1998

OTHER PUBLICATIONS

The Optimum Characteristcs of Dental Floss for Personal Oral Hygiene, Bass, Dental Items of Interest, 70, 921-934 (1948).

(Continued)

*Primary Examiner*—Todd E. Manahan
*Assistant Examiner*—Robyn Doan

(57) ABSTRACT

Disclosed are coated multifilament dental devices overcoated with biofilm-responsive, imbedded, particulate abrasives.

11 Claims, 10 Drawing Sheets

U.S. PATENT DOCUMENTS

| | | | | |
|---|---|---|---|---|
| 4,029,113 A | 6/1977 | Guyton | | 132/91 |
| 4,033,365 A | 7/1977 | Klepak et al. | | 132/89 |
| 4,034,771 A | 7/1977 | Guyton | | 132/91 |
| 4,151,851 A | 5/1979 | Bragg | | 132/91 |
| 4,215,478 A | 8/1980 | Thomas et al. | | 433/25 |
| 4,414,990 A | 11/1983 | Yost | | 132/91 |
| 4,548,219 A | 10/1985 | Newman et al. | | 132/91 |
| 4,610,872 A | 9/1986 | Lynch | | 424/49 |
| 4,612,242 A | 9/1986 | Vesley et al. | | 428/313.9 |
| 4,776,358 A | 10/1988 | Lorch | | 132/321 |
| 4,911,927 A | * 3/1990 | Hill et al. | | 424/443 |
| 4,950,479 A | 8/1990 | Hill et al. | | 424/49 |
| 5,032,387 A | 7/1991 | Hill et al. | | 424/49 |
| 5,033,488 A | 7/1991 | Curtis et al. | | 132/321 |
| 5,098,771 A | 3/1992 | Friend | | 428/209 |
| 5,163,975 A | 11/1992 | Martin | | 51/293 |
| 5,165,913 A | * 11/1992 | Hill et al. | | 424/49 |
| 5,194,297 A | 3/1993 | Scheer et al. | | 427/180 |
| 5,209,251 A | * 5/1993 | Curtis et al. | | 132/321 |
| 5,220,932 A | 6/1993 | Blass | | 132/321 |
| 5,226,435 A | 7/1993 | Suhonen et al. | | 132/321 |
| 5,232,775 A | 8/1993 | Chamberlain et al. | | 428/323 |
| 5,273,782 A | 12/1993 | Sagawa et al. | | 427/242 |
| 5,353,820 A | 10/1994 | Suhonen et al. | | 132/321 |
| 5,389,434 A | 2/1995 | Chamberlain et al. | | 428/323 |
| 5,423,337 A | 6/1995 | Ahlert et al. | | 132/321 |
| 5,502,216 A | 3/1996 | Mori et al. | | 549/310 |
| 5,503,842 A | 4/1996 | Fazan et al. | | 424/443 |
| 5,526,831 A | 6/1996 | Gilligan et al. | | 132/321 |
| 5,538,667 A | 7/1996 | Hill et al. | | 252/312 |
| 5,557,900 A | 9/1996 | Shaneour | | 52/736.3 |
| 5,560,377 A | 10/1996 | Donovan | | 132/321 |
| 5,561,959 A | 10/1996 | Alderman et al. | | 52/407.3 |
| 5,573,850 A | 11/1996 | Cunningham et al. | | 428/373 |
| 5,616,315 A | 4/1997 | Masterman et al. | | |
| 5,658,510 A | 8/1997 | Carraro et al. | | 264/70 |
| 5,665,374 A | 9/1997 | Hill et al. | | 424/435 |
| 5,711,935 A | 1/1998 | Hill et al. | | 424/49 |
| 5,718,251 A | 2/1998 | Gray et al. | | 132/321 |
| 5,765,576 A | 6/1998 | Dolan et al. | | 132/321 |
| 5,787,758 A | 8/1998 | Sheldon | | 74/490.07 |
| 5,830,495 A | 11/1998 | Ochs | | 424/443 |
| 5,848,600 A | 12/1998 | Bacino et al. | | 132/321 |
| 5,904,152 A | 5/1999 | Tseng et al. | | 132/321 |
| 5,908,039 A | 6/1999 | Ochs et al. | | 132/321 |
| 5,937,874 A | 8/1999 | Guay et al. | | 132/321 |
| 5,967,153 A | 10/1999 | Mitha et al. | | 132/321 |
| 5,967,154 A | 10/1999 | Anderson | | |
| 5,967,155 A | 10/1999 | Marcon | | 132/321 |
| 6,016,816 A | 1/2000 | Ariagno | | 132/321 |
| 6,026,829 A | 2/2000 | Mitha et al. | | 132/321 |
| 6,037,019 A | 3/2000 | Kooyer et al. | | 427/598 |
| 6,080,481 A | 6/2000 | Ochs et al. | | 428/372 |
| 6,080,495 A | 6/2000 | Wright | | 428/623 |
| 6,123,982 A | * 9/2000 | Fontana | | 427/2.29 |
| 6,221,341 B1 | 4/2001 | Montgomery | | 424/53 |
| 6,545,077 B1 | 4/2003 | Hill et al. | | 524/277 |
| 6,575,176 B1 | 6/2003 | Hill et al. | | 132/321 |
| 6,604,534 B1 | 8/2003 | Hill | | 132/321 |
| 6,609,527 B1 | 8/2003 | Brown | | 132/321 |

OTHER PUBLICATIONS

The role of local drug delivery in the management of periodontal diseases: a comprehensive review, Greenstein et al., J. Periodontol., May 1998, 69:5:507-520 (Abstract Only).

Metronidazole plus amoxycillin in the treatment of Actinobacillus actinomycetemcomitans associated periodontitis. van Winkelhoff et al., J. Clin. Periodontol., 1989, 16:128-131 (Abstract Only).

Susceptibility of oral bacterial biofilms to antimicrobial agents. Wilson, J. Med. Microbiol., 1996, 44 (2):79-87 (Abstract Only).

Biofilms, the Customized Microniche. Costerton et al., J. Bacterio., 1994, 176:2137-2142.

Cross-sectional studies in periodontal disease: current status and implications for dental practice. Douglass et al., Adv. Dent. Res., 1993, 7(1):25-31 (Abstract Only).

Periodontal response to mechanical non-surgical therapy: a review. Greenstein, Periodontol., 1992, 63 (2):118-130 (Abstract Only).

Physiological approaches to the control of oral biofilms. Marsh et al., Adv. Dent. Res., 1997, 11 (1):176-185 (Abstract Only).

Advances in the pathogenesis of periodontitis: summary of developments, clinical implications and future directions. Page et al., Periodont. 2000, 1997, 14:216-248.

Current and future approaches for diagnosis of periodontal diseases. Papapanou et al., NY State Dent. J., Apr. 1999; 65(4):32-7 (Abstract Only).

* cited by examiner

COATED MULTIFILAMENT DENTAL DEVICES OVERCOATED WITH IMBEDDED PARTICULATE

CROSS-REFERENCE TO RELATED APPLICATIONS

This application is a continuation-in-part of U.S. patent application, Ser. No. 10/073,682, filed 11 Feb. 2002, entitled, "Micromesh Interproximal Devices; and this application is related to copending U.S. patent applications, Ser. Nos. 10/331,795 and 10/334,089, each filed on the same date of this patent application, and entitled respectively, "Coated Monofilament Dental Devices Overcoated with Imbedded Particulate", and "Coated Multifilament Dental Devices Overcoated with Imbedded Particulate". The disclosures of these applications are hereby incorporated herein by reference.

BACKGROUND OF THE INVENTION

Dental floss is defined in *Webster's New World Dictionary*, 1983, as " . . . thread for removing food particles between the teeth."

The concept of using dental floss for cleansing interproximal spaces appears to have been introduced by Parmly in 1819, *Practical Guide to the Management of Teeth*, Cullins & Croft Philadelphia, Pa. Numerous types of floss were developed and used for cleaning interproximal and subgingival surfaces, until finally in 1948 Bass established the optimum characteristics of dental floss, *Dental Items of Interest*, 70, 921–34 (1948).

Bass cautioned that dental floss treated with sizing, binders and/or wax produces a "cord" effect as distinguished from the desired "spread filament effect". This cord effect reduces flossing efficiency dramatically and visually eliminates splaying (i.e., the flattening and spreading out of filaments) necessary to achieve the required interproximal and subgingival mechanical cleaning. This cleaning is then required to be followed by the entrapment and removal of debris, plaque and microscopic materials from interproximal spaces by the "spread" floss as it is removed from between teeth.

Proper use of dental floss is necessary to clean the considerable surface area on the interproximal surfaces of teeth, which cannot usually be reached by other cleaning methods or agents, e.g., the bristles of a toothbrush, the swishing action of a rinse, or by the pulsating stream from an oral irrigator.

Historically, the purpose of dental floss was to:
(1) dislodge and remove any decomposing food material, debris, etc., that has accumulated at the interproximal surfaces, which could not be removed by other oral hygiene means, and
(2) dislodge and remove as much as possible the growth of bacterial material (plaque, tartar, calculus) that had accumulated there since the previous cleaning.

Effective oral hygiene requires that three control elements be maintained by the individual:
(1) Physical removal of stains, plaque and tartar. This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.
(2) Surfactant Cleaning. This is required to remove: food debris and staining substances before they adhere to the tooth surface; normal dead cellular (epithelial) material which is continually sloughed off from the surfaces of the oral cavity and microbial degradation products derived from all of the above. Besides the obvious hygienic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth.
(3) Frequency of Cleansing. This is perhaps the most difficult to provide in today's fast-paced work and social environment. Most people recognize that their teeth should be brushed at least 3 times a day and flossed at least once a day. The simple fact is that most of the population brush once a day, some brush morning and evening, but precious few carry toothbrush and dentifrice to use the other three or four times a day for optimal oral hygiene. Consumer research suggests that the population brushes an average of 1.3 times a day. Most surprising, less than 15% of adults floss regularly. Reasons offered for not flossing: difficult to do, painful, not effective, doesn't seem to do anything, and leaves a bad taste.

It is generally accepted that multifilament dental floss is not a "user-friendly" product, i.e., it is difficult to do. It caused pain and bleeding and it results in a bad taste in the mouth. Most market researchers agree that anything that can be done to make flossing more positive should be implemented to encourage more frequent flossing and more wide spread floss use. The addition to floss of: full spectrum flavor oils, mouth conditioning substances such as silicones along with cleaners and abrasives that are perceived as "working" as taught by the present invention, are all sources of positive feed back to the flosser that would be considered encouraging and supportive. To achieve these requires basic changes in present floss manufacturing.

Three basic nylon fiber bundle constructions have been previously approved by the Food and Drug Administration (FDA) which has classified multifilament dental floss as a medical device. The three basic constructions are: 140 denier (68 filament) 100 denier (34 filament) and 70 denier (34 filament). Heretofore, 6 to 10 bundles of these three types were twisted together along with bonding agents to produce various commercial multifilament dental flosses.

Most commercial multifilament interproximal devices marketed at the present time contain various coatings of wax or wax like substances that function as: (1) binders for the various multifilament flosses to minimize fraying, (2) lubricants, (3) flavor carriers, and/or (4) fluoride carriers.

An almost universal shortcoming common to most waxed multifilament dental flosses is the user perception during flossing that the dental floss is "not working" and/or "not cleaning", etc.

In fact, most of these devices have only marginal efficacy with respect to removing biofilms (plaque). Biofilms generally require physical abrasive-type action to be effectively removed. Periodic professional cleaning is a recommended means for effectively controlling biofilm formation.

From 1960 thru 1982, numerous clinical studies reported that there is no clinical difference as to plaque removal and gingivitis scores between waxed and unwaxed multifilament dental floss. Note, both are "cord" flosses and contain sizing, binders, etc. These studies also confirmed that waxed and unwaxed floss are approximately 50% effective with respect to plaque removal and gingivitis scores. Thus the "cord" effect severely restricts efficiency of flossing and especially physical abrasive-type action associated with multifilament flosses that splay as described by Bass.

O'Leary in 1970, and Hill et al. in 1973, found no difference in the interproximal cleansing properties of waxed and unwaxed dental floss. This was reconfirmed in 1982 by Lobene et al. who showed no significant clinical difference on plaque and gingivitis scores. Similar results, i.e., no clinical difference between waxed and unwaxed multifilament dental floss with respect to reduced gingival inflammation were shown by Wunderlich in 1981. No differences in plaque removal were reported by Schmidt et al. in 1981 with multifilament flosses of various types. Stevens, 1980, studied multifilament dental floss with variable diameters and showed no difference in plaque and gingival health. Carter et al. 1975, studied professional and self administered waxed and unwaxed multifilament dental floss, both significantly, reduced gingival bleeding of interproximal and gingival sulci. Unwaxed multifilament dental floss appeared slightly, but not significantly more effective.

In view of this clinical work, it is not surprising that most of the multifilament dental floss sold today is contrary to the teaching of Bass, bonded and/or waxed. The "bonding" in the yarn industry today is used more to facilitate processing and production during multifilament dental floss manufacture and packaging than for "flossing" reasons. Since clinical tests show no difference between waxed and unwaxed multifilament dental floss (both unfortunately are "bonded"), the multifilament dental floss industry has been comfortable with the yarn industry's propensity to use bonding agents in multifilament dental floss, thereby sacrificing splaying and physical abrasive-type cleaning.

As noted above, there are three basic nylon strand constructions approved by the FDA for multifilament dental floss. These are 140 denier (68 filament), 100 denier (34 filament) and 70 (34 filament). Analysis of the commercial multifilament dental flosses sold worldwide show that almost all multifilament dental flosses available are twisted in generally the same manner, contain bonding agents, and are constructed by twisting several (6–10) strands selected from one of these three strand types.

The commercialization of the innovative multifilament dental flosses described and claimed in U.S. Pat. Nos. 4,911,927; 5,098,771; 5,165,913 and 5,711,935 to Hill et al. has extended the purpose of multifilament dental floss to include the release therefrom of chemotherapeutic agents, both interproximally and subgingivally. The efficacy of these new multifilament dental flosses has been documented in clinical studies reported in a filing responsive to the FDA call-for-data of Sep. 19, 1990, 55 Fed. Reg. 38560. See Docket No. 81N-0033, OTC 210246 to 210262. The Hill et al. patents and the referenced clinical studies are hereby incorporated herein by reference.

The Hill et al. patents teach that satisfactory multifilament dental flosses can be manufactured having loadings up to 100% of the substrate weight. These patents to Hill et al. taught that the floss loading weight could be extended beyond previous limits by positioning a cleaning preparation throughout the interior of the multifilament floss. More particularly, the patents to Hill et al. taught the deposition of a cleaning preparation in spaces between the several strands and between the individual filaments comprising each strand by a process called compression loading. The cleaning preparation activates as the floss splays upon being pulled between the teeth, thereby delivering the cleaning preparation to the oral cavity, especially the surfaces of the teeth.

The classification of plaque as a biofilm is considered a major advance in the development of more effective "self-treatment" oral care products. See the following biofilm references:

Greenstein and Polson, *J. Periodontol., May* 1998, 69:5: 507–520; van Winkelhoff, et al., *J. Clin. Periodontol.,* 1989, 16:128–131; and Wilson, *J. Med. Microbiol.,* 1996, 44:79–87.

Biofilms are defined as " . . . matrix-enclosed bacterial population adherent to each other and to the surface or intersurfaces. These masses secrete an exopolysaccharide matrix for protection. Considerably higher concentrations of drugs are needed to kill bacteria in biofilms than organisms in aqueous suspensions."

Costerton, J. W., Lewandowski, Z., DeBeer, D., Caldwell, D., Korber, D., James, G. Biofilms, the customized microniche. *J. Bacterio.,* 1994, 176:2137–2142.

The unique attributes of biofilms is being recognized as increasingly important in the 1990's. Future studies into the mode of growth of biofilms will allow manipulation of the bacterial distribution.

Douglass, C. W., Fox, C. H. Cross-sectional studies in periodontal disease: Current status and implications for dental practice. *Adv. Dent. Res.,* 1993, 7:26–31.

The number of adults over 55 who will need periodontal services will increase. The type of services will need to be adjusted to meet the need.

Greenstein, G. J., Periodontal response to mechanical non-surgical therapy: A review. *Periodontol.,* 1992, 63:118–130.

Mechanical therapy remains effective with caveats of compliance and skill of therapists.

Marsh, P. D., Bradshaw, D. J. Physiological approaches to the control of oral biofilms. *Adv. Dent. Res.,* 1997, 11:176–185.

Most laboratory and clinical findings support the concept of physiological control. Further studies will reveal details of biofilm diversity.

Page, R. C., Offenbacher, S., Shroeder, H., Seymour, G. J., Kornman, K. S. Advances in the pathogenesis of periodontitis: Summary of developments, clinical implications and future directions. *Periodont.* 2000, 1997, 14:216–248.

Genetic susceptibility to three oral anaerobic bacteria play an important part in the progression of periodontitis. Acquired and environmental risk factors exacerbate the problem. Mechanical disruption will remain an effective and essential part of periodontal therapy.

Papapanou, P. N., Engebretson, S. P., Lamster, I. B. Current and future approaches for diagnosis of periodontal disease. *NY State Dent. J.,* 1999, 32–39.

New techniques are available such as a novel pocket depth measurement device, microscopic techniques, immunoassay, DNA probes, BANA hydrolysis tests. These more clearly define the nature of periodontitis.

SUMMARY OF THE INVENTION

The present invention is directed to biofilm-responsive, coated multifilament dental flosses suitable for physical-abrasive-type removal, disruption and/or control of biofilms that form on interproximal and/or subgingival tooth surfaces not reachable by brushing or rinsing. The coated multifilament dental flosses of the present invention are overcoated with an imbedded particulate abrasive that remains substantive to the multifilament floss coating until said base coating in which it is imbedded is eventually released or partially disrupted from the multifilaments during flossing or remains as an effective abrasive throughout the use-life of the multifilament dental floss where the base coating on the floss is insoluble and remains substantive to the filaments during flossing.

During flossing, at the outset, the imbedded particulate abrasive overcoating functions as a "soft" abrasive version of an oral-type sandpaper removing, disrupting and/or controlling biofilms. Essentially the first pass through an interproximal space by the imbedded particulate, overcoated, multifilament dental floss results in a gentle "sandpaper" abrasive effect on the biofilms present, which effect is eventually followed by dissolving and/or breaking up of the waxed coating containing the particulate abrasive which is present on the multifilament strands. In another embodiment of the invention, insoluble base coating materials are used. These do not readily release from the multifilaments during flossing, and when impregnated with particulate abrasive, create a soft abrasive-type dental floss sandpaper, which is very effective in gently removing, disrupting and/or controlling biofilm throughout the use-life of the dental floss.

When a soluble base coating is used, the released wax/abrasive and/or particulate abrasive works in conjunction with the filaments of the floss to continue to remove, disrupt and/or control biofilms until the particulate abrasive is flushed away and/or dissolved by saliva. That is, the released particulate abrasive cooperates with the multifilament dental floss filaments as the floss is being worked interproximally and subgingivally to continue to deliver physical-abrasive-type cleaning, disruption and/or control of biofilms formed on interproximal and subgingival tooth surfaces.

The physical-abrasive-type cleaning, disruption and/or control of biofilms achieved with the various imbedded particulate abrasive overcoated multifilament dental flosses of the present invention continues until:

the multifilament dental floss is removed from the space and flossing of the area is discontinued, the particulate abrasive dissolves and/or is washed away, and/or the biofilm is physically removed, disrupted and/or controlled.

The physical-abrasive-type cleaning, disruption and/or control of biofilms with the imbedded particulate abrasive overcoated multifilament dental flosses of the present invention can be simultaneously improved further with a chemotherapeutic treatment by various chemotherapeutic substances contained in: (1) the base coating, (2) the particulate abrasive, and/or (3) other particulate overcoating substances used to introduce flavor, mouth feel, etc., attributes into the particulate overcoated multifilament dental flosses of the invention. In the latter version which is preferred, these chemotherapeutic substances are released onto the tooth surfaces during flossing along with the saliva soluble particulate that releases from the base coating.

Surprisingly, the particulate abrasive overcoating imbedded in the base coating on the multifilament dental floss of the present invention exhibits unexpected gentleness along with lower than expected abrasivity which, for purposes of the present invention, allows more abrasive particulates to be used in the overcoating, such as pumice, alumina, silica, etc. This "soft abrasive" effect is attributed in part to the cushion effect contributed by the base coating to the imbedded particulate abrasive. That is, the base coating containing the partially imbedded particulate abrasive tends to cushion the impact of the exposed portion of the abrasive particulate onto tooth surfaces during flossing. See FIG. 7. This "soft abrasive" effect is particularly important where insoluble base coatings are employed and the "sandpaper" effect continues over the use-life of a particular segment of the floss. In those instances where the abrasive/coating mixture breaks free from the multifilament strands during flossing, the base coating tends to help lubricate the particulate abrasive/multifilament combination reducing further the abrasivity of the particulate abrasive on tooth surfaces.

Accordingly, one embodiment of the present invention comprises biofilm-responsive multifilament dental floss devices.

A further embodiment of the present invention comprises coated multifilament dental floss devices with particulate abrasives imbedded in the coating thereby rendering the floss biofilm-responsive during flossing.

Another embodiment of the invention comprises a self-treatment means for routinely removing, disrupting and/or controlling biofilms formed on interproximal and subgingival tooth surfaces.

Still another embodiment of the invention comprises a method for overcoating coated multifilament dental flosses with imbedded particulate abrasives of various particle sizes and particle size distributions, in order to more effectively remove, disrupt and/or control biofilms.

Yet another embodiment of the invention comprises a patient self-treatment method for periodically removing, disrupting and/or controlling biofilms that form on interproximal and subgingival tooth surfaces.

A further embodiment of the invention comprises biofilm-responsive multifilament dental devices overcoated with imbedded particulate abrasives and containing a releasable wax-type base coating which contains an antimicrobial.

Another embodiment of the invention comprises biofilm-responsive multifilament dental devices overcoated with active imbedded particulate abrasives such as whitening and tartar control abrasives.

Still another embodiment of the invention comprises biofilm-responsive multifilament dental devices overcoated with imbedded dental particulate abrasives including silica, pumice, alumina, calcium carbonate and dicalcium phosphate dihydrate.

Yet another embodiment of the invention comprises biofilm-responsive, multifilament dental devices overcoated with imbedded particulate abrasives, where said abrasives contain other substances ranging from flavorants, antimicrobials and cleaning substances to mouth conditioners and various pharmaceutical substances.

A further embodiment of the invention comprises improved commercial, waxed, multifilament dental flosses with an overcoating of imbedded particulate abrasive.

Still another embodiment of the invention comprises improved commercial, waxed, multifilament dental flosses with overcoatings of imbedded particulate abrasive and saliva soluble particulate substances containing flavorant and mouth conditioning substances.

Another embodiment of the invention comprises improved commercial, waxed, multifilament dental flosses with an overcoating of imbedded particulate abrasive containing a saliva soluble, substance containing flavorant and mouth conditioners.

Yet another embodiment of the invention comprises a method for improving commercial waxed, multifilament dental flosses comprising sequential overcoating of said waxed multifilament dental flosses with two or more particulates having substantially different densities, wherein said various particulates are imbedded into the base coating prior to cooling and solidifying said base coating.

Still another embodiment of the invention comprises improved commercial, emulsion loaded, texturized, multifilament dental floss with an overcoating of imbedded particulate abrasive.

Another embodiment of the invention comprises improved commercial, wax coated, ultra-thin multifilament dental floss with an overcoating of imbedded particulate abrasive.

A further embodiment of the invention comprises a method to overcome the "cord" effect of waxed multifilament floss, while imparting physical abrasive properties to waxed flosses.

For purposes of describing the present invention, the following terms are defined as set out below:

The terms fiber and filament are used synonymously throughout this specification in a manner consistent with the first three definitions of "fiber" and the first definition of "filament" as given in the *New Illustrated Webster's Dictionary*, ©1992 by J. G. Ferguson Publishing Co. the relevant disclosure of which is hereby incorporated herein by reference.

The strength of the filaments may be expressed in terms of tenacity, defined as the force required to break the filaments, i.e., breaking force (in grams) divided by the filament basis weight (in denier). To prevent the floss filaments from breaking during use, the filaments generally have a tenacity of at least about 3 grams/denier, preferably at least about 5 grams/denier, and more preferably, at least about 7 grams per denier. Filaments which satisfy this tenacity requirement and which may be used in the multifilament floss of the invention include the polyamides, for example, nylon-6 and nylon-6,6; polyolefins, for example polypropylene and polyethylene; and polyesters such as polyethylene terephthalate and various natural products including cotton and silk.

"Multifilament dental devices" are defined as interproximal dental devices such as multifilament dental floss constructed of a bundle of fibers such as nylon, polypropylene, silk, etc. The particulate overcoated flosses of the invention are supple, by which we mean that they are soft, flexible and pliant. A supple multifilament floss is one which is gentle on the gums and hands, easy to hold, and slides easily between teeth because it complies to the curvature of tooth surfaces in order to fit between tight surfaces between the teeth. The factors that affect suppleness include filament basis weight (related to filament diameter), degree of twist, degree of entanglement and the elastic modulus of the material from which the yarn is made. As used herein, the term "basis weight" as used to describe filaments, yarns and flosses refers to the weight of the article (in grams) of 9000 meters of the article. The weight in grams of 9000 meters is sometimes referred to as "denier". For a given multifilament yarn, as the filament diameter decreases for a multifilament yarn of a given basis weight, the floss will be able to pass through tight spaces more easily because the individual filaments slide past each other. For example, a first floss may be comprised of a 630 denier, each filament having a basis weight of 6 denier. This yarn comprises 105 filaments. A second multifilament floss may be comprised of a second yarn also having a basis weight of 630 denier, each filament having a basis weight of 3 denier. This second yarn comprises 210 filaments. While both yarns have the same overall basis weight, multifilament floss made from the second yarn will pass more easily between the teeth because the smaller diameter filaments slide more easily past each other. Also, the smaller the filament diameter, the lower will be the bending modulus per filament and the bending modulus for the yarn as a whole, thereby making the multifilament floss softer and more flexible. As the degree of twist and/or entanglement of the yarn increases, the resulting multifilament floss becomes less supple because the filaments are unable to slide as the floss is inserted into tight interproximal spaces.

A measure of the "fineness" of the yarn comprising the multifilament floss of the invention is the yarn basis weight. The yarn basis weight (expressed in denier) affects such properties as the ease of passing between teeth, perception of cleaning between teeth, strength, and gentleness of the multifilament floss on the gums. As the overall basis weight of the yarn decreases, the multifilament floss will pass more easily between teeth. However, decreasing the basis weight below an acceptable value will decrease the floss strength, reduce the perception of cleaning between teeth and will be harsher on the gums. To balance these properties, the multifilament floss of the present invention preferably comprises a yarn having a basis weight of between about 500 and about 1200 denier. More preferably, the yarn should have a basis weight between about 550 and 850 denier, and most preferably, between about 550 and about 700 denier.

Examples of multifilament dental flosses suitable for purposes of the present invention are described in the following U.S. patents, which are hereby incorporated by reference:

| | | | | | |
|---|---|---|---|---|---|
| 4,911,927; | 4,029,113; | 4,610,872; | 4,034,771; | 5,908,039; | 2,667,443; |
| 3,830,246; | 1,149,376; | 1,069,874; | 5,830,495; | 2,748,781; | 1,138,479; |
| 1,839,486; | 1,943,856; | 6,080,481; | 2,700,636; | 3,699,979; | 3,744,499; |
| 3,837,351; | 4,414,990; | 3,330,732; | 5,967,155; | 5,937,874; | 5,505,216; |
| 5,503,842; | 5,032,387; | 4,950,479; | 5,098,711; | 1,989,895; | 5,033,488; |
| 2,542,518; | 2,554,464; | 1,285,988; | 1,839,483; | 4,151,851; | 2,224,489; |
| 2,464,755; | 02,381,142; | 3,800,812; | 3,830,246; | 3,897,795; | 3,897,796; |
| 4,215,478; | 4,033,365; | 3,771,536; | 3,943,949; | 6,016,816; | 6,026,829; |
| 5,353,820; | 5,557,900; | 5,226,435; | 5,573,850; | 5,560,377; | 5,526,831; |
| 5,423,337; | 5,220,932; | 4,548,219; | 3,838,702; | 5,904,152; | 4,911,927; |
| 5,711,935; | 5,165,913; | and | 5,098,711. | | |

Preferred multifilament dental devices include nylon, polyethylene, polypropylene, polyester, etc., flosses, including twisted, entangled, untwisted, untangled, texturized and versions thereof. Particularly preferred multifilament dental devices include various coated multifilament dental flosses such as detailed in Tables 3 through 5 below as well as those described and claimed in U.S. Pat. Nos. 4,911,927; 5,098,711; 5,165,913 and 5,711,935.

"Coatings" for the multifilament dental devices are defined as those substances that coat multifilament dental devices for purposes of: lubrication and ease of floss insertion for carrying flavors and other additives, providing "hand" so the device can be wound around the fingers, etc., such as described in detail in Tables 3 to 4 below. These coatings generally comprise from about 25 to about 100% by weight of the floss.

Preferred base coatings include:
  (1) insoluble, partially soluble and soluble wax coatings,
  (2) those emulsion coatings described in the following U.S. Pat. Nos. 4,950,479; 5,032,387; 5,538,667; 5,561,959; and 5,665,374, which are hereby incorporated by reference,
  (3) various dental floss coatings, such as described in U.S. Pat. Nos. 5,908,039; 6,080,495; 4,029,113; 2,667,443; 3,943,949; 6,026,829; 5,967,155 and 5,967,153, and (4) those saliva soluble coatings described and claimed in co-pending U.S. patent applications, Ser. No. 09/935,922, filed on Aug. 23, 2001, now U.S. Pat. No. 6,604,534; Ser. No. 09/935,920, filed on Aug. 23, 2001, now U.S. Pat. No. 6,545,077; Ser. No. 09/935,921, filed on Aug. 23, 2001, now U.S. Pat. No. 6,609,527; and Ser. No. 09/935,910, filed on Aug. 23, 2001, now U.S. Pat. No. 6,575,176.

"Particulate abrasives" are defined as saliva soluble, semi-soluble and insoluble abrasive substances having a wide range of particle sizes and particle size distribution.

Preferred particulate abrasives include various insoluble inorganics such as glass beads, and various insoluble organics such as particles of polyethylene, polypropylene, etc.

Particularly preferred inorganic particulate abrasives include various: (1) insoluble dental abrasives such as: pumice, silica, alumina, silicon dioxide, magnesium oxide, aluminum hydroxide, diatomaceous earth, sodium potassium aluminum silicate, zirconium silicate, calcium silicate, fumed silica, hydrated silica, and (2) soluble dental abrasives such as: dicalcium phosphate dihydrate, anhydrous dicalcium phosphate, sodium tripolyphosphate, calcium carbonate, etc. See also Table 1 below.

Particularly preferred "active" particulate abrasives include:
  peroxides such as: carbamide peroxide, calcium peroxide, sodium perborate, sodium percarbonate, magnesium peroxide, sodium peroxide, etc.; phosphates such as: sodium hexametaphosphate, tricalcium phosphate, etc.; and
  pyrophosphates such as: tetrasodium pyrophosphate, tetrapotassium pyrophosphate, sodium acid pyrophosphate, calcium pyrophosphate, etc. See also Table 2 below.

See also the following relevant U.S. Patents: U.S. Pat. Nos. 6,221,341; 3,491,776; 3,330,732; 3,699,979; 2,700,636; 5,220,932; 4,776,358; 5,718,251; 5,848,600; 5,787,758; and 5,765,576, which describe various oral care abrasives suitable for the present invention and are incorporated herein by reference.

"Releasable" particulate abrasive is defined as the property whereby particulate abrasive, which is imbedded into the base coating on multifilament dental floss, remains substantive to said base coating until flossing begins, after which time the imbedded particulate abrasive in the base coating eventually separates from the multifilaments along with the base coating which eventually dissolves and releases the particulate abrasive into saliva. Thus, the particulate abrasive remains available interproximally and subgingivally to work with the multifilament floss, responding to biofilms encountered on subgingival, interproximal and supragingival tooth surfaces with physical-abrasive-type cleaning.

Permanent and/or semi-permanent particulate abrasives are defined as those particulate abrasives imbedded in insoluble coatings which are generally not released from multifilament fibers during flossing.

"Particulate abrasive load" is defined as the percent by weight of imbedded particulate abrasive contained on the coated multifilament dental device as a percent by weight of the device. See Tables 1, 2, 3 and 5 below.

"Base coat multifilament device load" is defined as the percent by weight of the base coating contained on the multifilament device as a percent by weight of the coated multifilament device.

"Total coating load" is defined as the percent by weight of the base coating plus the particulate abrasive overcoating imbedded in said coating on the multifilament device as a percent by weight of the device.

"Perceived Abrasive Factor (PAF)" is defined as the subjective level of perceived abrasivity when:
  (1) winding the coated multifilament device with imbedded particulate abrasive around the fingers (i.e., "hand"), and
  (2) when working the device across tooth surfaces with a sawing action.

PAF grades range from 0 through 4, i.e., imperceptible (0), slightly perceptible (1), perceptible (2), very perceptible (3) and very abrasive (4). See Tables 1, 2 and 9 below. PAF values of about 2 or greater are preferred. PAF values above 3 are particularly preferred. Permanent abrasives generally exhibit higher PAF values than releasable abrasives.

"Incidental Release Factor (IRF)" is defined as the percent by weight of the particulate abrasive retained on the coated multifilament dental device, when an 18 inch piece of the device is removed from a dispenser and wrapped around two fingers prior to flossing. (See Tables 1, 2 and 9.) IRF values over 90% reflect the degree to which the particulate abrasives are imbedded in the base coating, as well as the tenacity of this imbedded particulate in the solidified base coating. When a cross-section of a bundle of filaments is viewed under a microscope, it is apparent that from between about 20 to about 90% of the total surface of each particulate is imbedded into the base coating on the multifilaments. This extent of particulate surface imbedding into the base coating is primarily responsible for the "it's working" perception which registers during flossing along with the particulate abrasive retained during handling of the floss prior to flossing (IRF). Permanent abrasives generally exhibit higher IRF values than releasable abrasives.

"Biofilm responsive" is defined as the property of particulate abrasives and saliva soluble particulates to work cooperatively with multifilament dental flosses and other cleaning and/or chemotherapeutic substances in the base coating to remove, disrupt and/or control biofilms during flossing.

"Fluidized bed" is defined as a means of converting solid particulate abrasives into an expanded, suspended, solvent-free mass that has many properties of a liquid. This mass of suspended particulate abrasive has zero angle of repose, seeks its own level, while assuming the shape of the containing vessel.

"Sequential fluidized beds" are defined as a means of converting solid particulate abrasives and solid particulate saliva soluble substances separately into expanded, suspended, solvent-free masses that have many properties of a liquid. These separate fluidized masses of suspended particulate abrasive and suspended solid, saliva soluble substances each have zero angle of repose and seek their own level, while assuming the shape of the containing vessel.

DETAILED DESCRIPTION OF THE PREFERRED EMBODIMENTS

Figure 1:
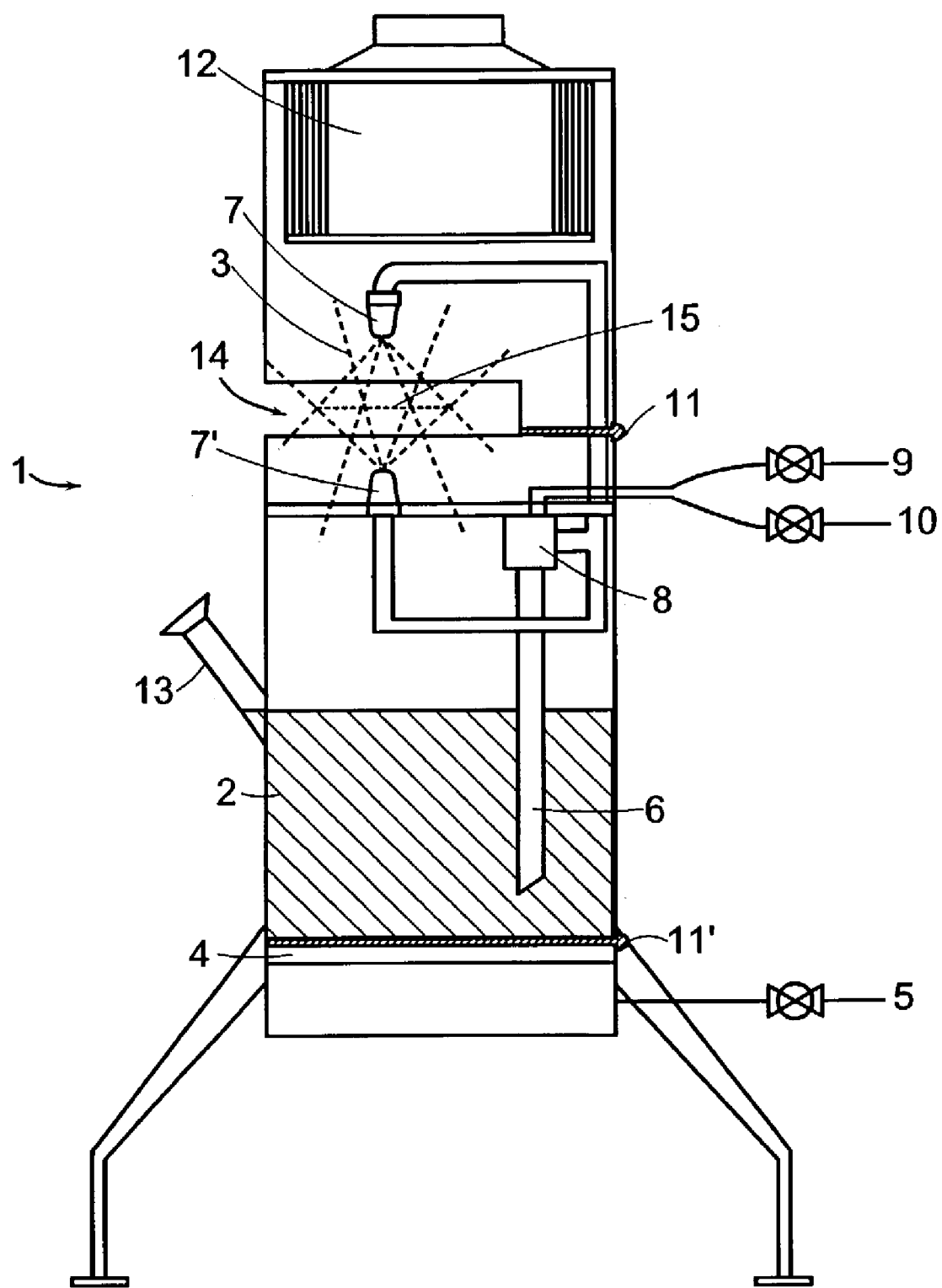
FIG. 1 is a schematic side view of a particulate overcoating system of the invention suitable for overcoating wax-type coated multifilament devices with imbedded particulate abrasive and imbedded, saliva soluble, solid substances containing flavorants, mouth conditioners, nutraceuticals and/or active therapeutic ingredients.

Referring to FIG. 1 which is a schematic side view of a particulate abrasive overcoating system comprising: particulate coating system, 1, consisting of fluidized bed means, 2, comprising: fluidized particulate abrasive, 3, membrane, 4, fluidizing air means, 5, stand pipe, 6, in communication with particulate abrasive nozzle means, 7, provided with pump means, 8, which contains nozzle air input means, 9, and pump cleaning means, 10.

Figure 1A:
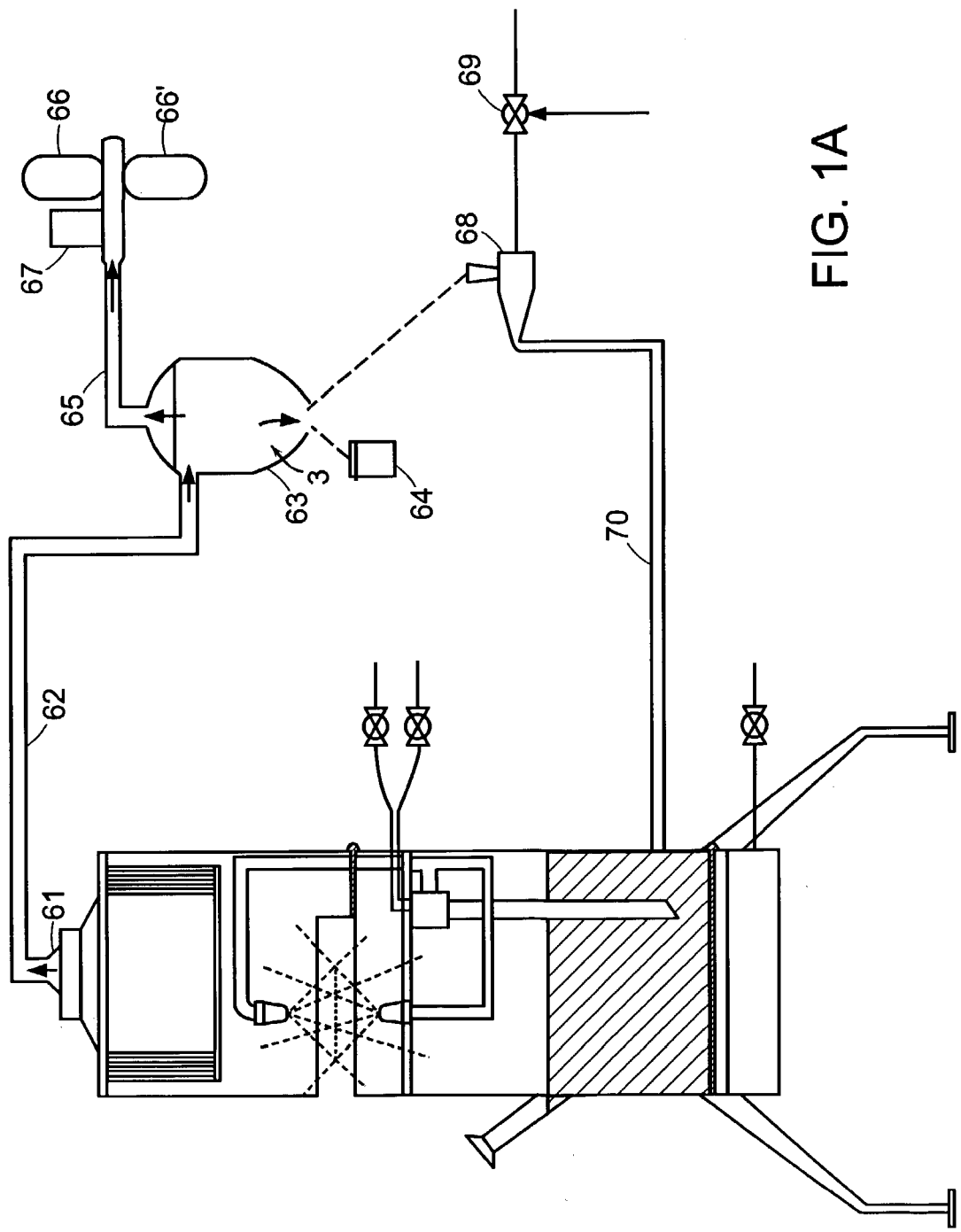
FIG. 1A is a schematic side view of a particulate overcoating system as shown in FIG. 1, with the filter means replaced by fitted with means to recover the particulate overspray that does not contact the multifilament during the overcoating operation.

Particulate coating system, 1, is provided with hinged access means, 11 and 15, and filter means, 12, particulate filling means, 13, and coated multifilament dental floss particulate coating zone, 14, and coated multifilament dental flosses, 15. Filter means, 12, can be assisted by a vacuum cyclone means which capture all unused particulate, 3, overspray and recycles same. This is detailed in FIG. 1a.

Coated multifilament dental floss, 15, with a liquid coating contained thereon, passes through particulate coating zone, 14, where particulate, 3, is imbedded into the liquid coating on multifilament dental floss, 15, from nozzle means, 7.

Referring to FIG. 1, vacuum cyclone means, 60, replaces former filter means, 12, and is connected to the top of particulate coating system, 1, at juncture 61, via tubing means, 62. Vacuum cyclone means, 60, maintains a slight negative pressure within particulate coating system, 1, by drawing air and some dispersed particulate from coating system, 1, and introducing this air/particulate mixture into vacuum cyclone chamber, 63, where particulate, 3, is introduced into holding means, 64, and the remaining air substantially free from particulate, 3, passes through the top of chamber, 63, through tubing, 65, via motor, 67, into filter means, 66 and 66'. Alternatively, particulate, 3, is captured by collecting means, 68, with air regulator, 69, and returned to particulate coating system, 1, via tubing, 70.

Figure 2:
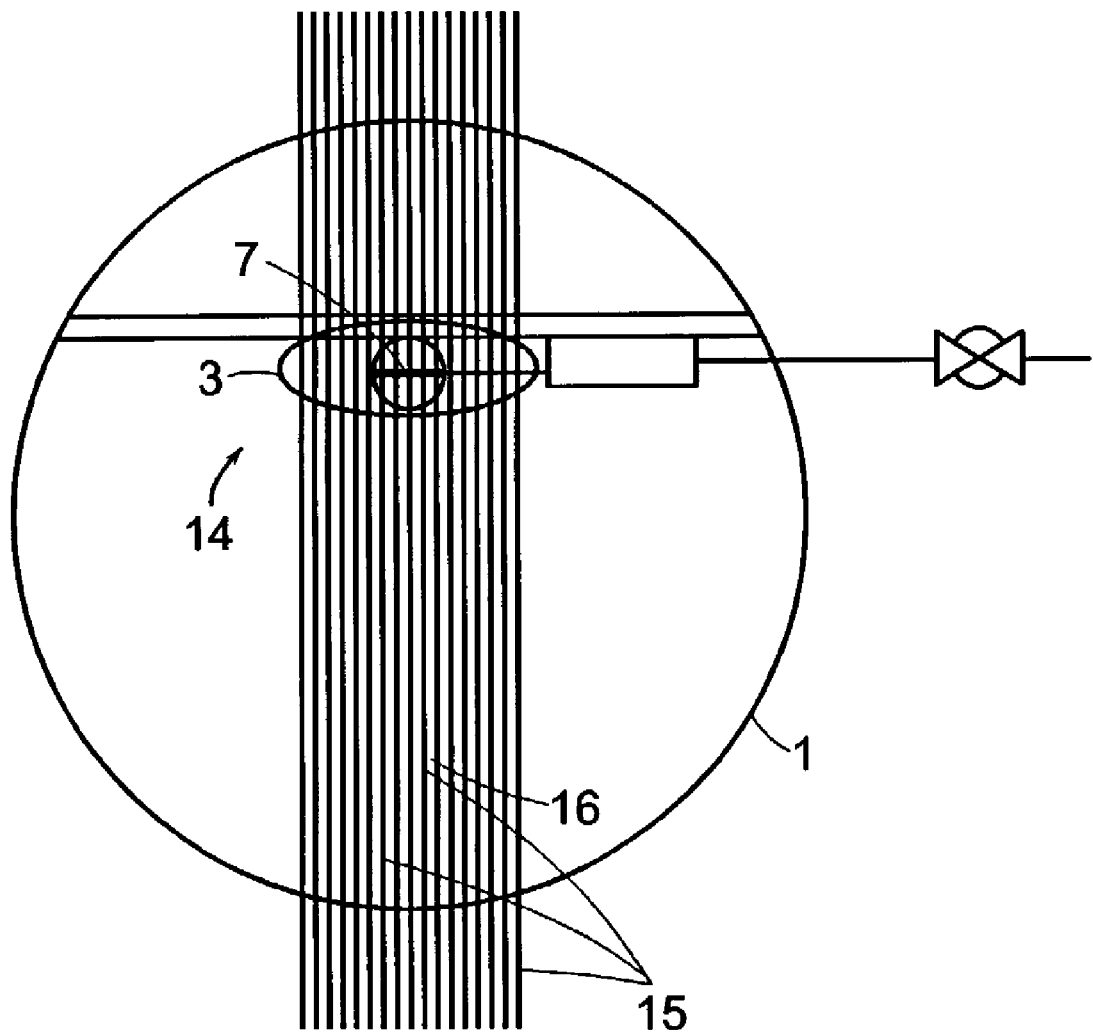
FIG. 2 is an enlarged top view of the system shown in FIG. 1 showing wax-type coated multifilament dental floss passing through the particulate coating chamber.

Referring to FIG. 2, which is an enlarged top view of particulate coating system, 1. Multifilament dental floss, 15, with liquid base coating, 16, thereon, passes through particulate coating zone, 14, where particulate abrasive, 3, from nozzle means, 7, is imbedded via impinging into liquid base coating, 16, which is substantive to the multifilament dental floss, 15, as multifilament dental floss, 15, passes through particulate coating zone, 14.

Figure 3:
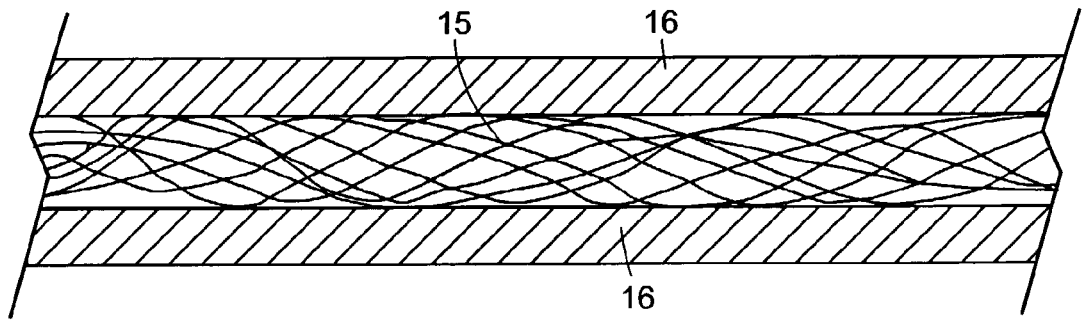
FIG. 3 is an expanded, schematic, cross-sectional view of a coated multifilament dental device showing a liquid wax-type coating on the multifilament dental floss prior to the coated floss entering the particulate coating chamber.

Referring to FIG. 3, which is an expanded, schematic, cross-sectional view of coated multifilament dental floss, 15, showing base wax-type liquid coating, 16, thereon before the floss, 15, passes into particulate coating zone, 14. The base wax-type coating, 16, has been heated and is in a liquid state and is substantive to the multifilament floss filaments, 15.

Figure 4:
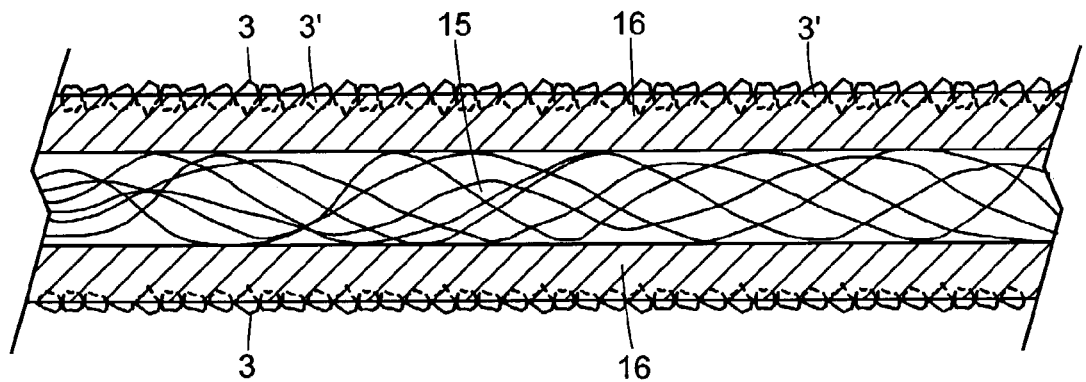
FIG. 4 is an expanded, schematic, cross-sectional view of wax-type coated multifilament dental floss showing particulate abrasive imbedded into the liquid wax-type coating after the multifilament dental floss passes through the particulate abrasive coating chamber.

Referring to FIG. 4, which illustrates an expanded, schematic, cross-sectional view of wax-type coated multifilament floss, 15, showing base liquid coating, 16, containing particulate abrasives, 3, imbedded into the liquid coating, 16, with the imbedded portion of the particulate abrasive shown via dotted lines designated as 3'.

Figure 5:
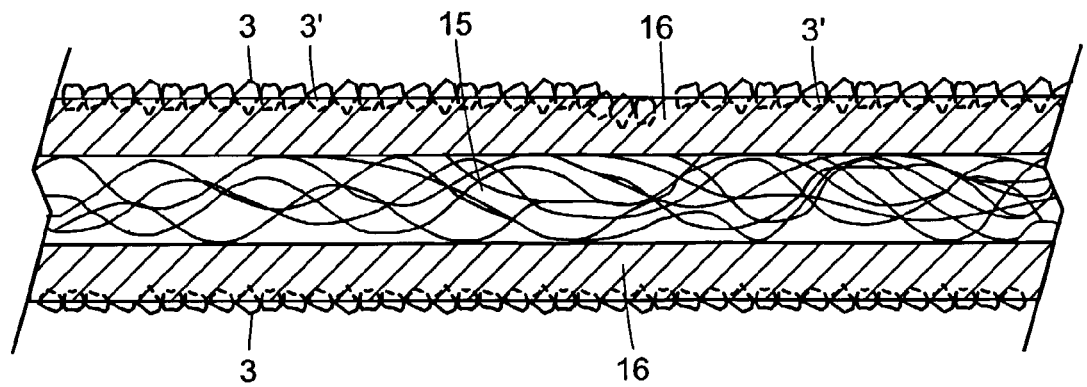
FIG. 5 is an expanded, schematic, cross-sectional view of a wax-type coated multifilament dental floss showing particulate abrasive partially imbedded into the solidified wax-type coating after the particulate abrasive overcoated, multifilament dental floss has been passed through a cooling zone, thereby solidifying the wax-type coating (the cooling zone is not shown).

Referring to FIG. 5, which is an expanded, schematic, cross-sectional view of wax-type coated multifilament dental floss, 15, showing base coating, 16, that has been passed through a cooling zone (not shown) sufficient to solidify said base coating, 16, with particulate abrasive, 3, firmly imbedded into said solidified base coating, 16, with the imbedded portion of the particulate abrasive represented by the dotted lines designated as 3'.

Referring to FIGS. 1 and 5, in a particularly preferred embodiment of the invention, the particulate overcoating system set forth in FIG. 1 is replicated and in line, in order to sequentially imbed two distinct particulate substances having substantially different densities onto the liquid base coating, 16, on multifilament, 15. Under this sequential particulate coating operation, particulate abrasive, 3, imbeds into coating, 16, prior to the particulate overcoated floss, 15, passing directly from a first particulate coating zone, 14, into a second similar particulate abrasive coating zone, where a high impact particulate is also imbedded into base coating, 16, prior to the particulate overcoated floss, 16, passing to the cooling zone, not shown. In this sequential arrangement, two distinct particulates having substantially dissimilar densities are imbedded into the liquid base coating, 16, using this sequential fluidized bed arrangement prior to said base coating solidifying.

Figure 6:
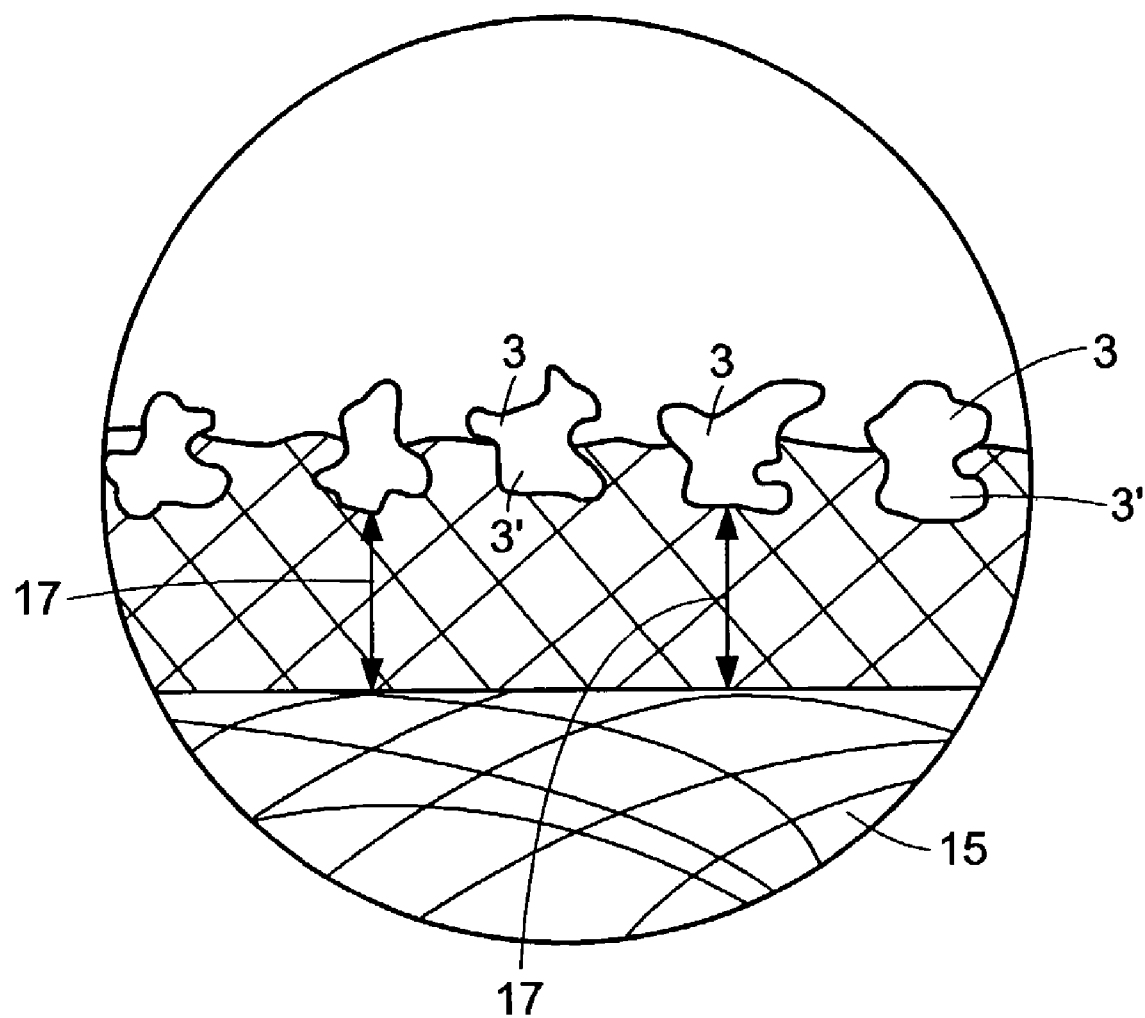
FIG. 6 is a blown up schematic, cross-sectional view of coated multifilament dental floss showing particulate abrasive partially imbedded into the solidified wax-type coating which functions as a cushion for the abrasive.

Referring to FIG. 6, which is an expanded, schematic, longitudinal, cross-sectional view of wax-type coated multifilament dental floss, 15, showing solidified base coating, 16, with particulate abrasive, 3, firmly partially imbedded in solidified wax-type base coating, 16, with "cushion", 17, extending from the bottom of particulates, 3', to the surface of multifilament dental floss, 15. The imbedded portion of the particulate abrasive is designated as 3'.

Figure 7:
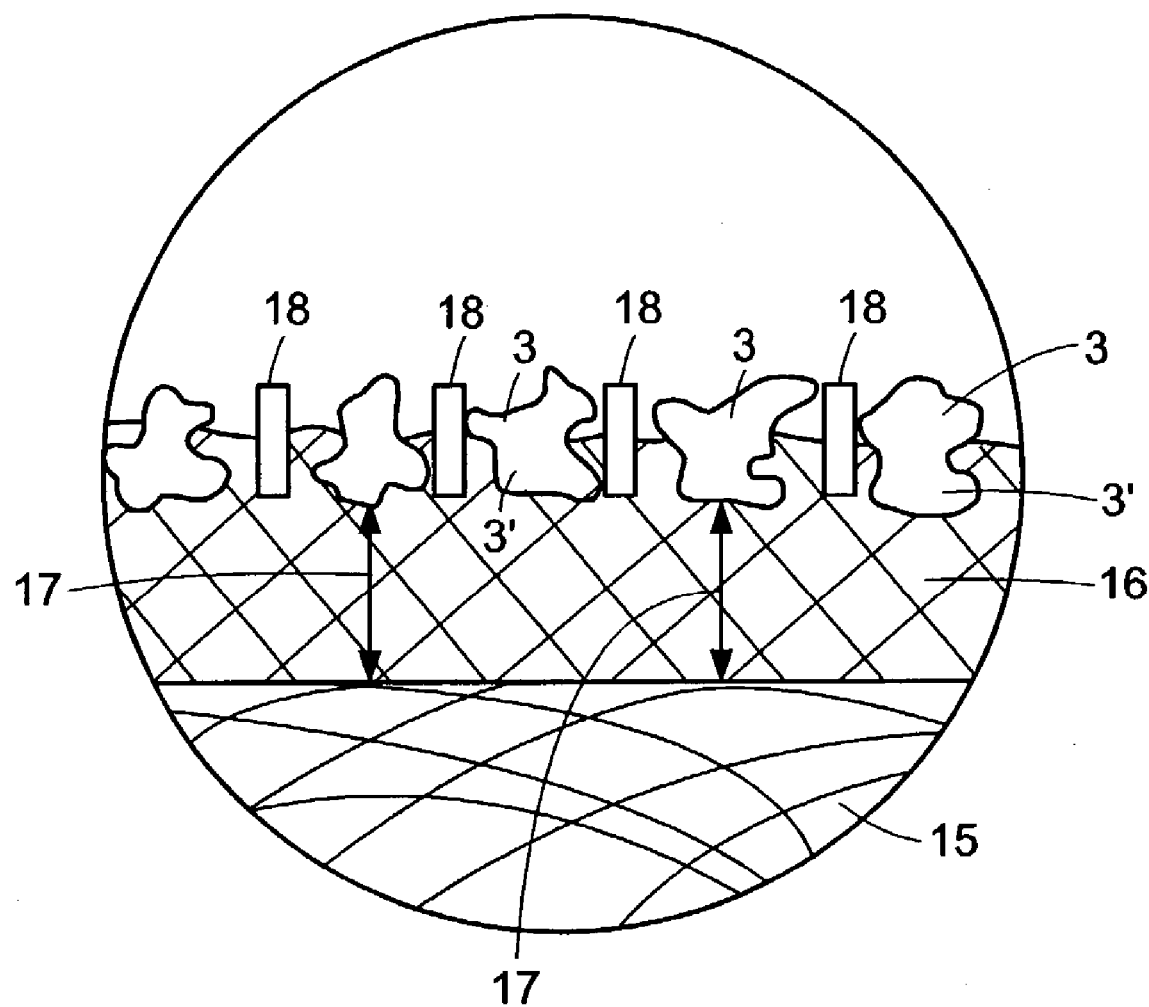
FIG. 7 is a blown up schematic, cross-sectional view of coated multifilament dental floss showing a mixture of particulate abrasive and saliva soluble flavor/mouthfeel containing particulates partially imbedded into the solidified wax-type base coating.

Referring to FIG. 7, which is an expanded, longitudinal, cross-sectional view of wax-type coated multifilament dental floss, 15, showing a mixture of particulate abrasive, 3, and saliva soluble particulate, mouth feel, mouth conditioning, substance, 18, each shown firmly partially imbedded into said solidified base coating, 16.

Figure 8:
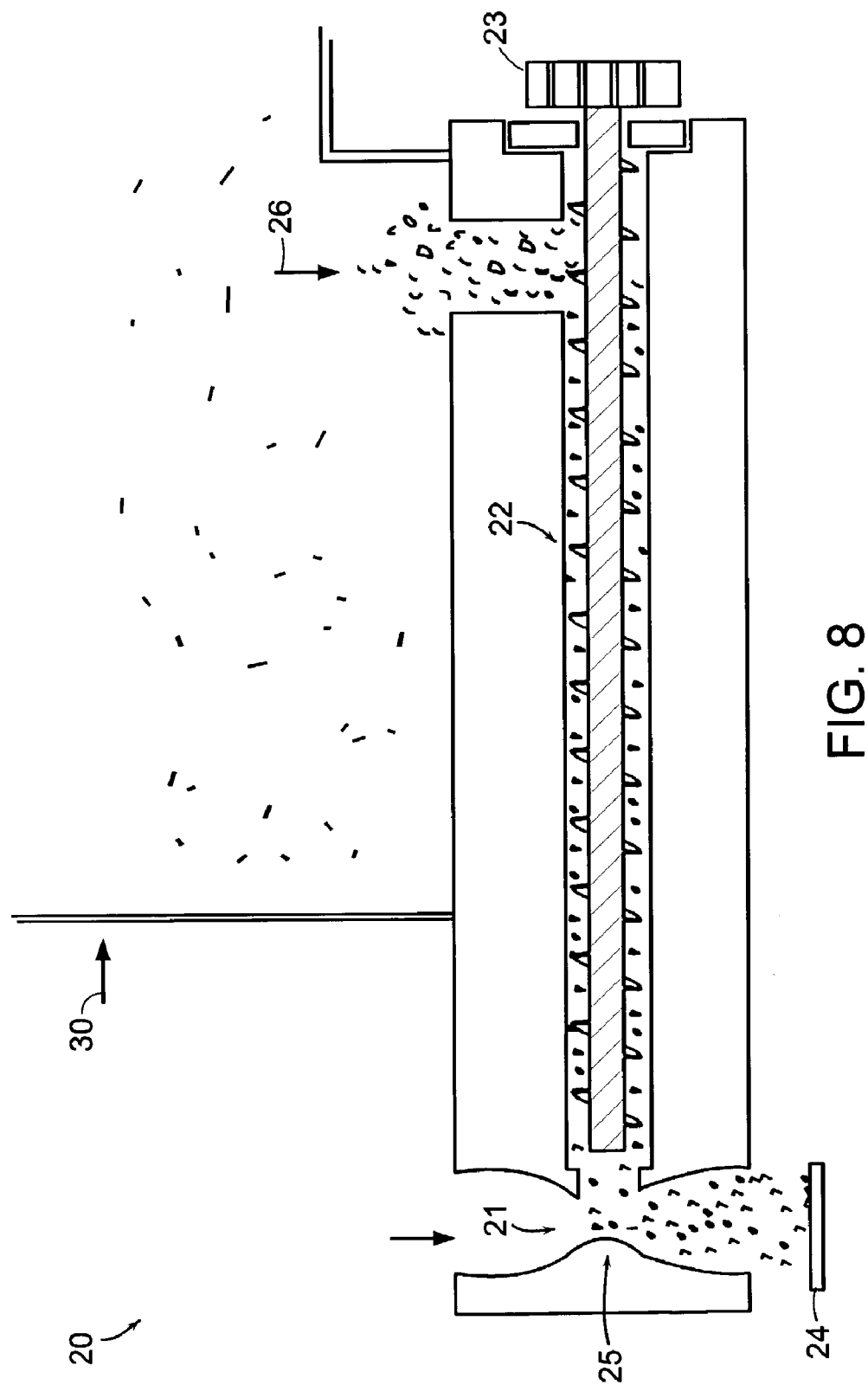
FIG. 8 is a schematic side view of an alternative particulate overcoating system of the present invention suitable for overcoating wax-type coated multifilament devices.

Referring to FIG. 8, which is a schematic side view of an alternative particulate overcoating system, 20, for delivering a particulate, 21, from a vessel or fluidized-bed means, 30, to a conveying agent means, 22, with gear drive means, 23. The speed of conveying auger, 22, is controlled by motor driven gear means, 23, which is slaved to a surface speed controller, not shown, for multifilament floss, 24. As the multifilament floss, 24, moves faster, auger means, 22, speeds up and delivers more particulate, 21, to the surface of molten-coated multifilament floss, 24. This system then allows for the delivery of a constant density of particulate, 21, per square millimeter of multifilament floss, 24. This alternative particulate overcoating system requires substantially lower volumes of air with corresponding reductions in overspray of particulates. This system requires minimal recovery of unused particulate and/or recycling of unused particulates.

In the foregoing system, the particulate, 21, may be an abrasive such as pumice, having an average particulate size of 37 microns which are fluidized with a porous plate of sintered polyethylene powder of 0.5 inch thickness. The plate has an average pore size of 20 microns. As the fluidized pumice is presented to auger means, 23, it is pulled down the shaft and presented to venturi means, 25. Control of the air flow in proportion to the speed allows uniform delivery of pumice to a surface of multifilament floss, 24, passing under the outlet of venturi means, 25. This arrangement allows delivery of uniform particle density with very low air speed, consistent with little perturbation of the floss traverse.

Figure 9:
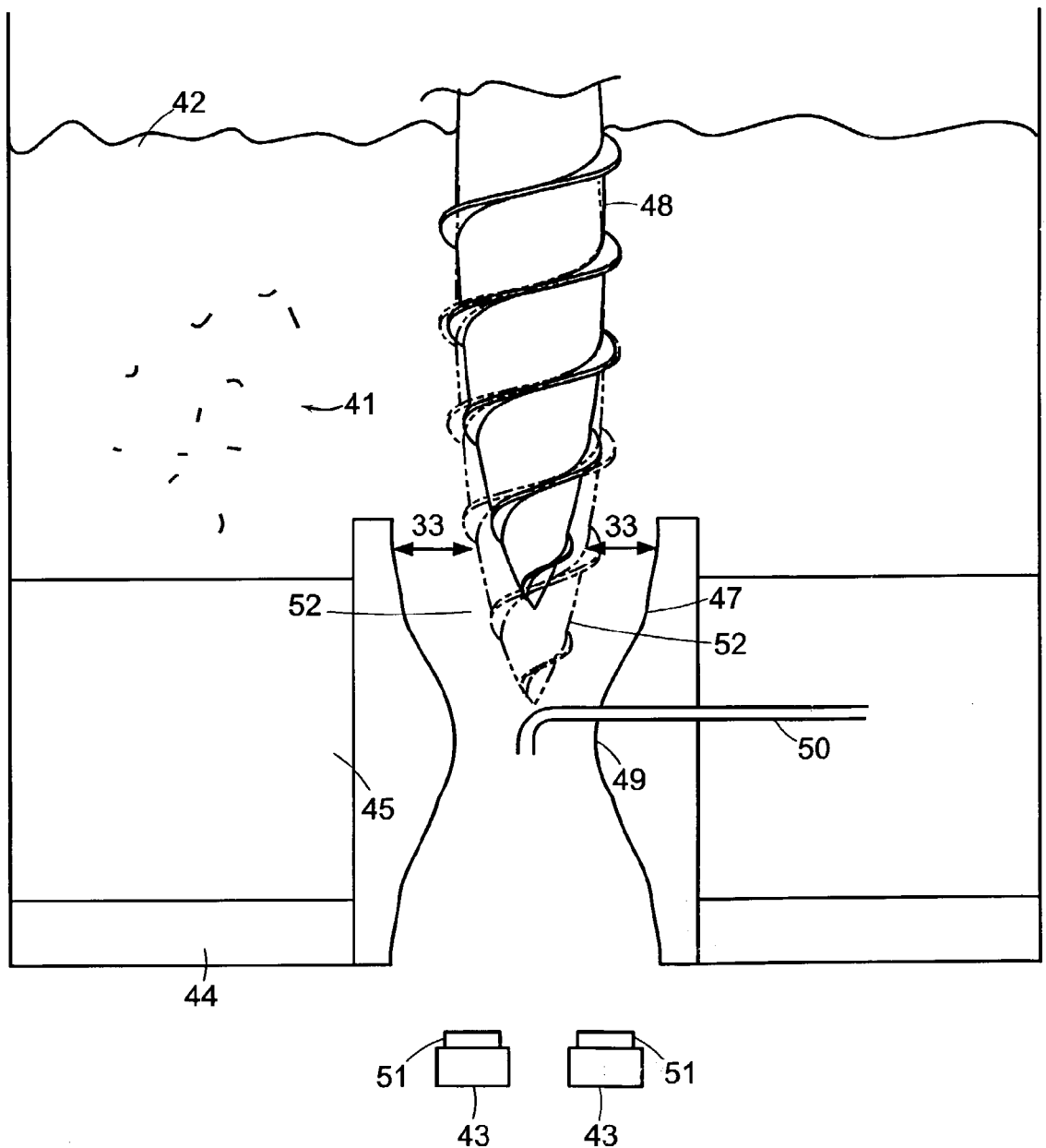
FIG. 9 is a schematic side view of another alternative particulate overcoating system of the present invention suitable for overcoating wax-type coated multifilament devices, where the particulate used for overcoating is not detailed.
Figure 10:
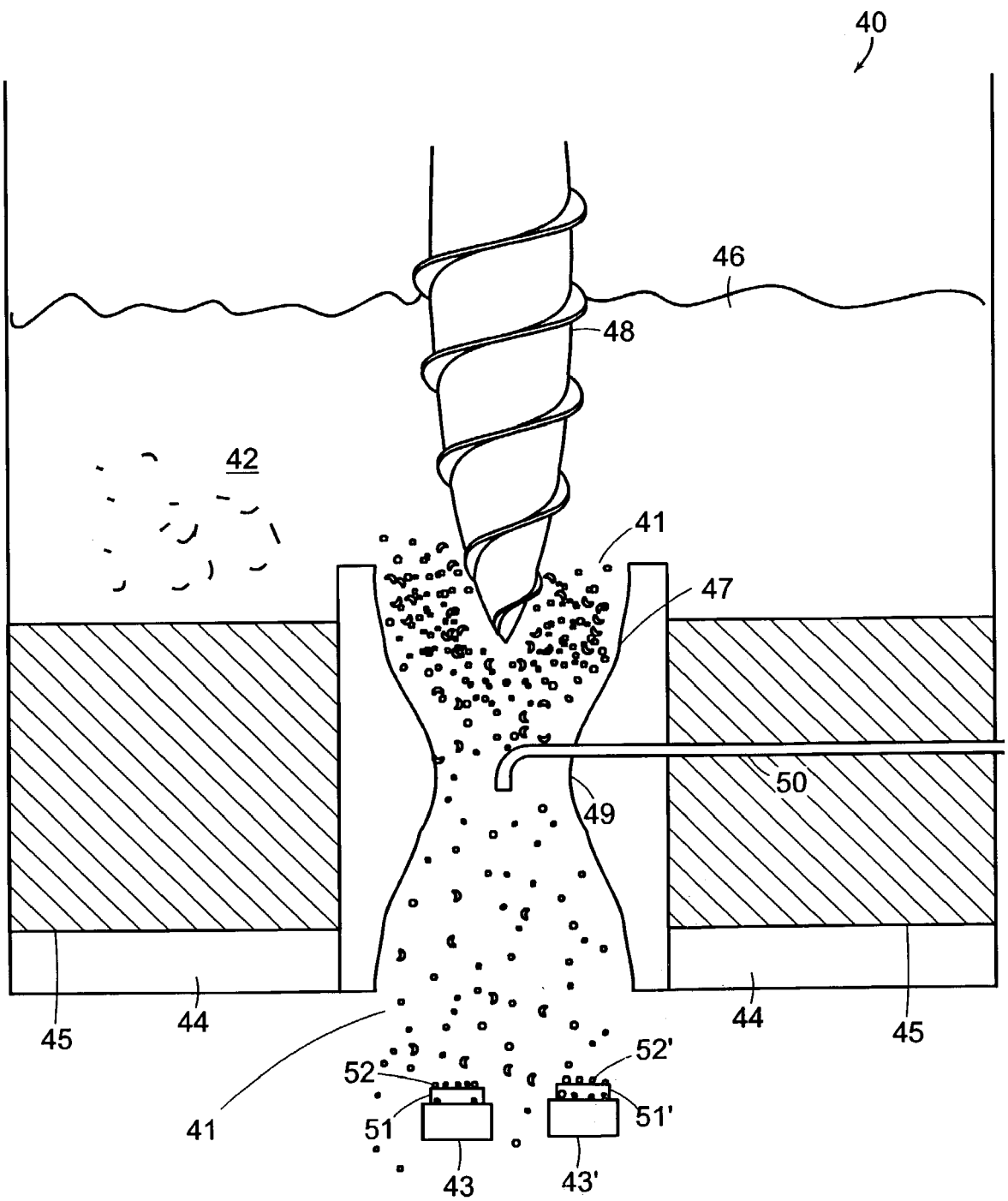
FIG. 10 is similar to FIG. 9, with the particulate used for overcoating shown in detail.

Referring to FIGS. 9 and 10, which are two separate schematic side views of another alternative particulate overcoating system, 40, for delivering particulates, 41, from a fluidized bed means, 42, to multifilament flosses, 43 and 43'.

Air chamber means, 44, introduces air under low pressure through distributor plate means, 45, which in turn fluidizes particulates, 41, in fluidized bed means, 46. Particulates, 41, are introduced from fluidized bed, 46, into particulate coating chamber, 47, by particulate metering means, 48. Particulate coating chamber, 47, is provided with venturi means, 49. Modulating particulate dispensing means, 50, is provided with high velocity, low volume air means (not shown) providing turbulence to fluidized particulate, 41, prior to said particulate imbedding coatings, 51 and 51', on the multifilament floss filaments, 43 and 43', respectively. Particulate dispensing means, 50, enhances the uniformity of the particulate, 41, overcoating, 52 and 52', imbedded into coatings, 51 and 51', respectively.

Referring to FIG. 9, generally the pressure in air chamber, 44, is between 4 and 8 psi. Distributor plate, 45, is preferably a porous polyethylene means that creates air bubbles required to fluidize particulates, 41, in fluidized bed, 42. The air pressure in fluidized bed, 42, is preferably in the 0.2 to 0.5 psi range. Particulate metering means, 48, can take many shapes other than that of the threaded means depicted. For example, metering means can be a plug or ram without threads that controls the flow of particulates, 41, from fluidized bed, 42, into particulate coating chamber, 47. Lowering metering means, 48, into particulate coating chamber, 47, as shown by dotted lines, 52, further restricts the flow of fluidized particulate, 41, through distance, 53. Thus, particulate metering means, 48, determines the quantity of fluidized particulate, 41, to enter particulate metering area, 47. This control in combination with modulated air flow through particulate dispersing means, 50, produces a substantially uniform density particulate on coating, 51, with imbedded particulates, 52, being dispersed substantially uniformly throughout coating, 51.

For a production system comprising up to 32 multifilament lines running side-by-side, the particulate overcoating system, 40, will be replicated in groups of 8, with two such groups covering the total of 32 lines running side-by-side.

Figure 11:
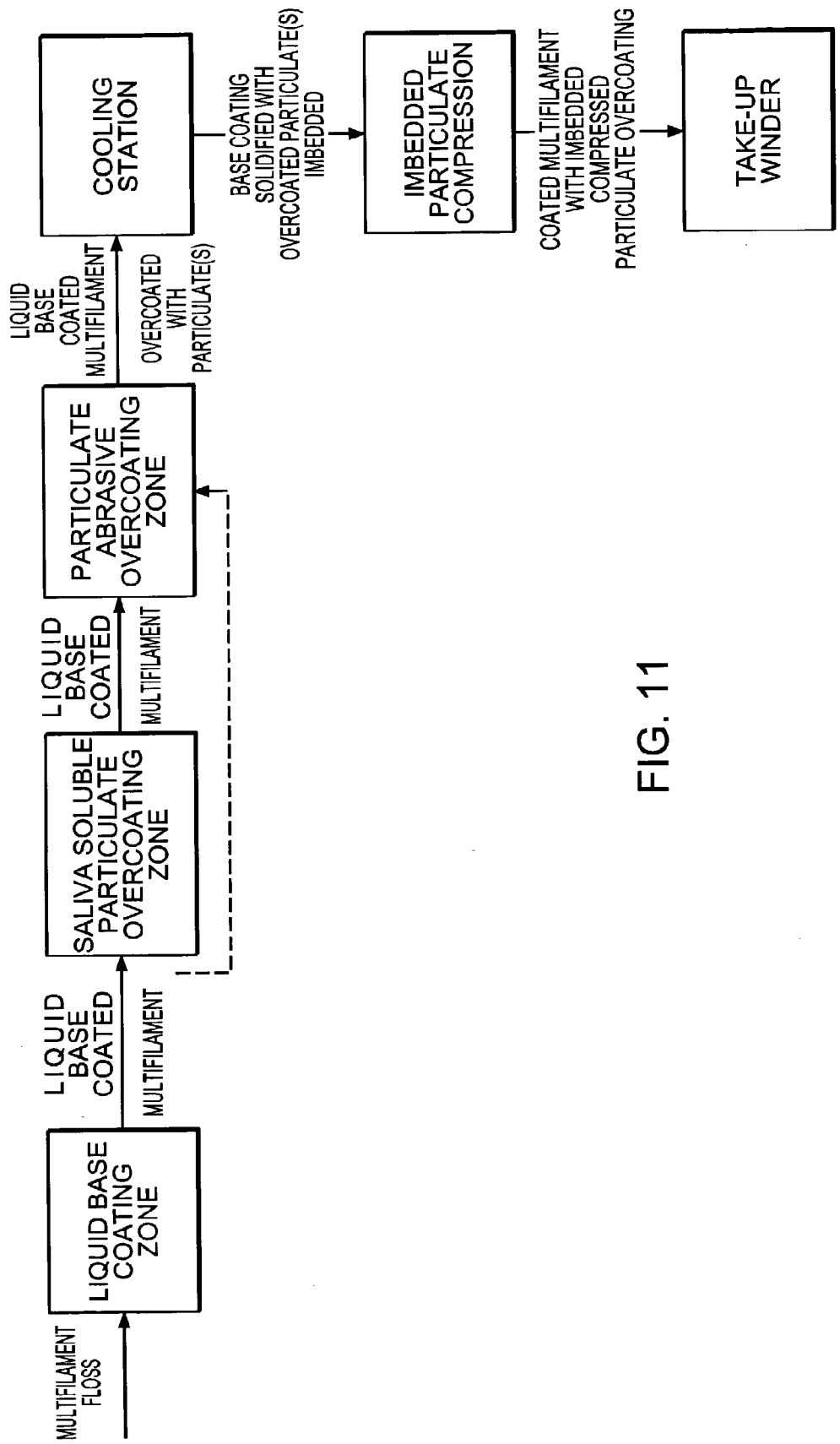
FIG. 11 is a schematic flow chart for particulate overcoating of coated multifilament dental floss.

Referring to FIG. 11, which is a schematic flow chart for particulate overcoating of coated multifilament dental floss, multifilament floss is passed through liquid base coating zone where the base coating is applied. Particulate overcoating is applied by introducing the coated multifilament into one or two particulate overcoating zones, after which the particulate overcoated multifilament floss passes through a cooling zone, followed by passing the overcoated multifilament through a particulate compression means before being introduced to a take-up winder means. In a preferred embodiment, the particulate overcoating system is provided with a particulate recovery means such as detailed in FIG. 1a.

The multifilament dental floss used in the present invention preferably comprises:

a bundle of multi-fiber dental floss wherein:

the multi-fiber dental floss:

contains from between 2 and 12 bundles, has a denier between about 300 and about 1,200, and contains between about 100 and about 800 filaments;

the fibers include natural and/or man made fibers and mixtures thereof including filament bundles with tackings throughout, twisted continuous filament bundles and texturized multifilament bundles, each of which can be comprised of nylon, polyester, polypropylene, cotton, silk, etc., and blends thereof; and Bundles of multi-fiber dental floss, as described above, with specific functionality such as adsorption wherein:

the multi-fiber, multi-composition dental floss:

contains 1–6 bundles of the specific functionality fibers, has a specific functionality fiber denier between 50 and 500, which contains between 20 to 400 filaments.

Preferably the multi-composition portion of the multi-fiber dental floss includes:

swellable fibers such as used in disposable diapers, saliva or water soluble fibers containing additional chemotherapeutic preparations, hollow membrane transport fibers such as are used in dialysis systems, microporous fibers such as Accurel® fibers by AKZO Chemie constructed from polyethylene or polypropylene, fibers rendered essentially microporous by the incorporation of micron-sized particles of calcium carbonate, talc, etc., and fibers capable of withdrawing water or specific fluids by incorporating micron-sized particles of agents such as calcium chloride, silica gel, activated charcoal and the like.

In a preferred embodiment of the present invention the multifilament dental floss used is nylon which contains between 4 and 8 bundles with a denier between about 500 and about 1,000 and contains between about 200 and 600 filaments, with or without texturizing. In a particularly preferred embodiment of the present invention the dental floss used is nylon containing 6 bundles and has a denier of about 840 with approximately 408 filaments.

The particulate abrasives and other saliva soluble particulate substances of the present invention are imbedded into the coated multifilament dental floss base coatings as solid materials totally free from solvents.

A preferred method of imbedding particulate abrasive overcoatings and saliva soluble particulate overcoatings into the coated multifilament device is by means of a series of innovative fluidized bed systems such as the system shown in FIG. 1.

Membrane means, 4, is used to maintain the particulate abrasive, 3, or saliva soluble particulate, 18, in a state of continued fluidization, i.e., fluidized bed, 2. Particulate abrasive, 3, or saliva soluble particulate, 18, can each be maintained in a fluidized state using fluidizing bed, 2. These fluidized particulates are introduced essentially at a 90° angle to the traverse of coated multifilament dental floss, 15, via nozzle means, 7 and 7', through stand pipe means, 6, via pump means, 8.

Referring to FIG. 2, coated multifilament dental floss, 15, passes through particulate coating zone, 14, and is imbedded with particulate abrasive, 3, as shown in FIGS. 4 thru 6, or with saliva soluble particulate, 18, as shown in FIG. 7. Particulate abrasive, 3, and saliva soluble particulate, 18, are each separately introduced under high impact conditions into liquid base coating, 16, on multifilament floss, 15, via nozzle means, 7 and 7', via separate particulate overcoating system positioned sequentially in a series immediately prior to the particulate overcoated multifilament flosses entering the cooling zone, not shown.

Imbedding of the particulate abrasive, 3, into the wax-type coating, 16, throughout the coating on the multifilament, 15, is achieved by means of impinging said particulate into the hot, liquid, wax-type, base coating that is present over the entire outer surface of said multifilament device at the time the particulate abrasive, 3, impinges the coating, 16. See FIGS. 4 thru 6.

That is, the particulate abrasive, 3, impinges into liquid coating, 16, which is substantive to filament, 15, as the device passes through particulate coating zone, 14, and particulate abrasive, 3, is imbedded into coating, 16, as shown in FIG. 5 and in solidified coating, 16, as shown in FIGS. 6 and 7.

That is, particulate abrasive, 3, impinges into the hot, viscous base coating, 16, which is a viscous liquid generally at a temperature between about 48° C. and 110° C. with a viscosity between 10 and 10,000 cs. This is illustrated in FIGS. 4 and 5, with the exposed portion of particulate abrasive designated as 3, and the imbedded portion of the particulate abrasive indicated by dotted lines and designated as 3'.

The multifilament dental floss overcoated with imbedded particulate then proceeds through a cooling means (not shown), where the base coating, 16, cools and solidifies with the particulate abrasive, 3, imbedded therein, as illustrated in FIGS. 5 through 7.

FIG. 7 illustrates a high-impact embodiment of the particulate abrasive overcoating into a multifilament dental floss base coating. That is, the particulate abrasive, 3, and particulate saliva soluble substances that contain mouth conditioners, flavorants, active ingredients, etc. This "hi-impact" particulate overcoating includes both particulate abrasive and particulate saliva soluble substances containing mouth conditioners and/or flavorants, both of which are imbedded into the base coating as illustrated in FIG. 7. Referring to FIG. 7, a mixture of particulate abrasive, 3 and 3', along with saliva soluble particulate substance, 18, are sequentially imbedded into base coating, 16, on multifilament floss, 15, from separate fluidized bed sources prior to base coating, 16, solidifying.

The overcoatings of particulate abrasive and various saliva soluble particulate substances containing flavorants and/or mouth conditioners and/or chemotherapeutic substances can include a broad range of these substances. For example, particulate ratios of particulate abrasives to saliva soluble substances such as nonionic surfactants (PLURONICS), emulsions such as MICRODENT® and/or ULTRAMULSIONS® and/or polyols such as PEG in these hi-impact particulate overcoatings can range from 10:90 to 90:10.

The innovative fluidized bed coating process of the present invention is most effective in imbedding:

(1) particulate abrasive loads between about 2 and about 45 percent by weight into the coated device, (2) particulate, saliva soluble loads between about 2 and about 45% by weight into the coated device, (3) particulate abrasive overcoating into coated multifilament devices with a perceived abrasive factor (PAF) between about 2 and 4, and (4) particulate abrasive, overcoating into coated multifilament devices with an Incidental Release Factor (IRF) value well above 80%, and preferably over 90%, and most preferably over 95%.

It has been discovered that in order to produce a coated multifilament dental device with PAF values in the 3 to 4 range, it is necessary: (1) to embed particulate abrasive loads at between about 10 and 34 percent by weight of the device, (2) to restrict the average particle size of the imbedded particulate abrasive to between about 7 microns and about 200 microns, (3) to restrict the particle size distributions of the imbedded particulate abrasive to from between about 5 microns and about 300 microns, and (4) to imbed the particulate abrasive into the liquid base coating under a high velocity charge from several nozzle means positioned at 90° to the traverse of the coated multifilament floss through the particulate coating chamber, thereby maximizing the impingement of the particulate abrasive into the base coating.

Overcoating coated multifilament floss with saliva soluble particulate can be carried out by imparting a static charge to the saliva soluble particulate prior to discharge from the nozzle means. Means are provided for grounding the liquid, base, coated multifilament in order to receive the charged saliva soluble particulate. Alternatively, saliva soluble particulate can be imbedded into liquid base coatings on multifilament dental flosses by various spraying means.

In addition to various types of fluidized bed/nozzle arrangements, the particulate abrasive overcoatings can be imbedded into the coated multifilament dental flosses by several other means for impinging particulate abrasives onto liquid coated multifilaments. These include various powder coating processes including fluidized bed, plastic frame-spraying, electrostatic spraying and sonic spraying. In the latter, sound waves are used to suspend the particulate abrasives before introducing the fluidized particulate abrasive into a nozzle means. Other particulate abrasive overcoating processes are described in U.S. Pat. Nos. 6,037,019; 3,848,363; 3,892,908; 4,024,295; 4,612,242; 5,163,975; 5,232,775; 5,273,782; 55,389,434; 5,658,510; 2,640,002; 3,093,501; 2,689,808; 2,640,001 and 5,194,297. These can be adapted to particulate abrasive impingement on coated multifilament as taught by the present invention and are incorporated herein by reference.

Particularly preferred particulate overcoating means include various Nordson® automatic powder coating systems such as the Nordson® Tribomatic II powder coating system, which includes various Nordson® powder pumps, as well as ITW Gema Powder coating systems including their Easysystem™ and Electrostatic Equipment Co's 7R FLEXICOAT® system.

The particulate overcoating of the invention can be affected with various other means for delivering particulate to the liquid base coating. For example, the particulate can be introduced by a simple screening technique where the particulate drops from the screening means onto the liquid means onto the liquid base-coated multifilament.

The preferred means of the invention for overcoating includes a fluidized bed in combination with a nozzle means. This combination provides the most uniform overcoatings while controlling the extend of the particulate imbedding into the liquid base coating and optimizing PAF and IRF values.

Various dental particulate abrasives imbedded into a standard coated multifilament dental floss having an average denier of 840 and a base coating of about 25 mg/yd, suitable for purposes of the present invention, are illustrated in Examples 1 through 7, as described in detail in Table 1 below:

TABLE 1

"Dental" Particulate Abrasives suitable for imbedding into coated multifilament dental flosses

| Example # | Particulate Abrasive(s) | Avg. Particle Size (in microns) | Particle Size Distribution (in microns) | Particulate Abrasive Load as % by wt. of device | Projected Incidental Release Factor (IRF) in % | Projected Perceived Abrasive Factor (PAF) | Estimated % of total particulate abrasive surface area imbedded into coated multifilament floss |
|---|---|---|---|---|---|---|---|
| 1 | pumice | 35 | 4–120 | 23 | 95 | 3.5 | 14 to 19 |
| 2 | silica | 10 | 2–18 | 10 | 98 | 1.5 | 6 to 9 |
| 3 | pumice & silica | 12 | 2–120 | 16 | 96 | 2.5 | 13 to 15 |
| 4 | dicalcium phosphate dihydrate | 55 | 18–100 | 15 | 98 | 1.5 | 12 to 14 |
| 5 | alumina | 25 | 10–75 | 20 | 94 | 3.7 | 15 to 18 |
| 6 | calcium carbonate | 50 | 15–80 | 16 | 97 | 2.0 | 13 to 15 |
| 7 | polyethylene | 20 | 8–40 | 12 | 98 | 1.5 | 9 to 11 |

Various "active" particulate abrasives imbedded into a standard coated multifilament dental floss having a denier of 840 and containing about 30 mg/yd base coating, suitable for purposes of the present invention, are illustrated in Examples 8 through 12 as described in detail in Table 2 below:

TABLE 2

"Active" Particulate Abrasives suitable for imbedding into coated multifilament dental flosses

| Example # | Particulate Abrasive(s) | Avg. Particle Size (in microns) | Particle Size Distribution (in microns) | Particulate Abrasive Load as % by wt. of device | Projected Incidental Release Factor (IRF) in % | Projected Perceived Abrasive Factor (PAF) | Estimated % of total particulate abrasive surface area imbedded into coated multifilament floss |
|---|---|---|---|---|---|---|---|
| 8 | tricalcium phosphate & silica | 60 | 10–150 | 10 | 90 | 3.0 | 7 to 9 |
| 9 | tetrapotassium pyrophosphate & pumice | 65 | 20–175 | 12 | 90 | 2.5 | 8 to 11 |
| 10 | tetrasodium pyrophosphate | 70 | 20–150 | 8 | 90 | 2.5 | 5 to 7 |
| 11 | sodium hexametaphosphate & pumice | 75 | 20–175 | 17 | 85 | 3.0 | 12 to 15 |
| 12 | calcium pyrophosphate & silica | 9 | 4–35 | 20 | 98 | 2.0 | 15 to 19 |

Suitable particulate abrasives for the present invention can also contain active ingredients "dusted" thereon. For example, antimicrobials such as cetylpyridinium chloride, triclosan, chlorhexidine, etc., can be dusted onto the particulate abrasives prior to overcoating the coated multifilament floss. During flossing, these antimicrobial coatings on the particulate abrasives are released therefrom during flossing and remain available interproximally and subgingivally to work with the particulate abrasive imbedded multifilament dental floss during flossing as biofilms are being removed, disrupted and/or controlled.

Wax is a preferred base coating. The term wax is used as a generic classification of many materials that are either natural or synthetic, and generally these materials are considered wax-like because of their functional characteristics and physical properties. They are solid at ambient temperatures with a relatively low melting point, and capable of softening when heated and hardening when cooled. In general, the higher the molecular weight of a wax, the higher is the melting point.

Waxes are usually classified by their source as natural or synthetic waxes. The waxes obtained from natural sources include animal waxes, such as beeswax; vegetable waxes such as candelilla and carnauba; mineral waxes and petroleum waxes such as paraffin and microcrystalline wax. The synthetic waxes include Fischer-Tropsch waxes, polyethylene waxes, fatty acid waxes and amide waxes.

One preferred embodiment of the invention employs certain insoluble waxes coated onto multifilament flosses. These insoluble waxes do not readily release and/or break away from the fibers during flossing. When impregnated with particulate abrasive, these insoluble waxes continue to impart the "soft abrasive" sandpaper effect throughout the flossing procedure.

Natural Waxes:

Petroleum waxes are, by far, the largest markets of the naturally occurring waxes. Petroleum waxes are further classified into paraffin and microcrystalline waxes.

Paraffin wax is obtained from the distillation of crude oil, and consists mainly of straight-chain saturated hydrocarbons. The molecular weight ranges from 280 to 560 (C20 to C40) and the melting point is about 68° C.

Microcrystalline wax is produced by deoiling the petrolatums or greases obtained by dewaxing deasphalated residual lube stocks or by deoiling the deasphalated tank bottoms that settle out during the storage of crude oil. These waxes are referred to as microcrystalline because the crystals are much smaller than those of paraffin wax. Microcrystalline waxes are composed predominantly of isoparaffinic and naphthenic saturated hydrocarbons along with some n-alkanes. The molecular weight ranges from 450 to 800 (C35 to C60), and produced in two grades with lower (65° C.) and higher (80° C.) melting points.

Animal Waxes are Usually of Insect or Mammalian Origin.

Beeswax is one of the most important commercially available animal waxes and is derived from honeycomb by melting the comb in boiling water and skimming off the crude wax. It is composed of nonglyceride esters of carboxylic and hydroxy acids with some free carboxylic acids, hydrocarbons and wax alcohols. The melting point of this wax is about 62–65° C. with a flash point of 242° C.

Vegetable waxes are obtained either from leaves and stems or from fruits and seeds. Candelilla and carnauba waxes are the most important commercial vegetable waxes.

Candelilla wax is composed of hydrocarbons (50%), nonglyceride esters, alcohols and free acids. It has a low volume expansion or contraction upon phase change, and melts at about 68–72° C.

Carnauba wax is the hardest and highest melting point of the vegetable waxes. It is composed primarily of nonglyceride esters with small amounts of free acids, resins and hydrocarbons. It melts at about 83–86° C.

Synthetic Waxes:

Fischer-Tropsch wax is a by-product in the synthesis of liquid fuels, such as gasoline and diesel oils, obtained by catalytic hydrogenation of carbon monoxide at high temperature and pressure. It is composed of n-alkanes in the molecular weight range of 600–950 with a melting point of 95–120° C.

Polyethylene wax, with molecular weights of 2,000–10,000, have properties of high molecular weight hydrocarbon waxes. These low densities, low molecular weight polyethylenes are made by high-pressure polymerization, low-pressure polymerization with Zeigler-type catalysts, or by thermal degradation of high molecular weight polyethylene. They have a melting point of 90–120° C.

Synthetic grades of beeswax, candelilla and carnauba waxes are also available with similar properties as the natural grades.

Water-Soluble Waxes:

Polyethylene glycol, polymers of ethylene oxide, in the form of relatively low molecular weight liquids and waxes, are commonly referred to as poly polyethylene glycol-13 (PEG). Typically, polymers with molecular weight below 20,000 are defined as PEG and those above 20,000 are polyethylene oxide-(PEO). PEGs are available in molecular weights ranging from 1,000 to 20,000, and are all water-soluble. The solubility decreases with increases in molecular weight. The melting point of PEG varies from 45–60° C. depending on molecular weight.

Tables 3 and 4 below describe in detail various coatings suitable for coating multifilament flosses and suitable for imbedding with the particulate particles of the present invention. Key compliance factors, such as Gentleness, Hi-impact Flavor and Mouth Feel of these overcoated multifilament dental flosses are attributed in part to the various base coatings such as described in Table 4, Examples 25 through 39 and to the various saliva soluble particulate substances imbedded into the base coating. The particulate abrasive overcoatings imbedded into these coated multifilament flosses impart the unexpected perception that the floss "is working", a key compliance factor.

TABLE 3

Suitable Wax Coatings for Various Multifilament Dental Flosses

| Ex. No. | Multifilament Floss-Type Denier (filament) | Multifilament Processing: twists/inch [tacking/yd], etc. | Wax Base Coating Type (mg/yd) | Imbedded Particulate Abrasive-Type (mg/yd) | Projected IRF (in %) | Projected PAF (in %) | Estimated % of total particulate abrasive surface area imbedded into wax coating |
|---|---|---|---|---|---|---|---|
| 13 | Nylon 6,6 140 (408) | 2.4 | microcrystalline wax (28) | pumice (20) | 92 | 3.6 | 17 to 24 |
| 14 | Nylon 6,6 140 (408) | 1.6 | microcrystalline wax (34) | pumice (12) | 98 | 3.2 | 13 to 16 |
| 15 | Nylon 6,6 140 (408) | 1.6 | microcrystalline wax (34) | pumice (16) | 96 | 3.4 | 15 to 18 |
| 16 | Nylon 6,6 140 (408) | 1.6 | microcrystalline wax (34) | Silica (15) | 98 | 2.8 | 19 to 26 |
| 17 | Nylon 6,6 140 (408) | 1.6 | microcrystalline wax (34) | Silica (9) | 99 | 2.5 | 15 to 18 |
| 18 | Nylon 6,6 140 (408) | 1.6 | Bees wax (24) | Pumice (20) | 94 | 3.5 | 16 to 25 |
| 19 | Nylon 6,6 140 (408) | 1.6 | Bees wax (24) | Pumice (11) | 97 | 3.1 | 12 to 16 |

TABLE 3-continued

Suitable Wax Coatings for Various Multifilament Dental Flosses

| Ex. No. | Multifilament Floss-Type Denier (filament) | Multifilament Processing: twists/inch [tacking/yd], etc. | Wax Base Coating Type (mg/yd) | Imbedded Particulate Abrasive-Type (mg/yd) | Projected IRF (in %) | Projected PAF (in %) | Estimated % of total particulate abrasive surface area imbedded into wax coating |
|---|---|---|---|---|---|---|---|
| 20 | Nylon 6,6 140 (408) | 1.6 | Bees wax (24) | Silica (16) | 98 | 2.5 | 18 to 20 |
| 21 | Polyethylene 660 (220) | 1.6 | PEG 3350 (30) | Pumice (21) | 90 | 3.7 | 18 to 26 |
| 22 | Polyethylene 660 (220) | 1.6 | PEG 3350 (30) | Pumice (13) | 95 | 3.2 | 13 to 18 |
| 23 | Polyethylene 660 (220) | 1.6 | PEG 3350 (30) | Pumice (9) | 98 | 2.9 | 10 to 13 |
| 24 | Polyethylene 660 (220) | 1.6 | Bees wax (27) | Pumice (18) | 94 | 3.6 | 16 to 23 |

Suitable emulsion, saliva soluble and flake-free base coatings for various multifilament dental flosses are described in Examples 25 through 39 in Table 4 below:

TABLE 4

Suitable Base Coatings other than Wax for Multifilament Dental Flosses to be overcoated with particulate abrasive

| Ingredients | 25 | 26 | 27 | 28 | 29 | 30 | 31 | 32 | 33 | 34 | 35 | 36 | 37 | 38 | 39 |
|---|---|---|---|---|---|---|---|---|---|---|---|---|---|---|---|
| Ultramulsion 10/2.5 | | | 57.4 | | 52.1 | 49.4 | 56.9 | | 64.8 | 45.4 | | | | 77.1 | 78.6 |
| Microwax 445 | | | 7.0 | | 7.0 | 7.0 | 7.2 | | | 7.0 | | | | | |
| PEG 40 Sorbitan diiso. | | | 3.0 | | 3.0 | 3.0 | 3.0 | | | 3.0 | | | | | |
| Stearyl alcohol | | | 15 | | 15 | 15 | 15 | | | 15 | | | | | |
| Insoluble saccharin | 2.3 | 1.6 | 1.3 | 1.0 | 2.1 | 1.8 | 1.8 | 2.3 | 2.3 | 1.8 | 2.3 | 2.3 | 2.3 | 2.1 | 2.3 |
| Propyl Gallate | 0.1 | 0.1 | 0.1 | 0.1 | | 0.1 | 0.1 | 0.1 | 0.1 | 0.1 | 0.1 | 0.1 | 0.1 | | 0.1 |
| Flavor | 9.6 | 10.0 | 10.0 | 7.5 | 5.4 | 8.5 | 10.0 | 8.8 | 8.6 | 10.0 | 4.0 | 4.0 | 8.0 | 6.0 | 6.0 |
| Dicalcium dihydrate phosphate | | | 6.0 | | | | 3.0 | 13.3 | | | 15.0 | | | | 13.0 |
| Pumice | | | | | | | 3.0 | | | | | | | | |
| EDTA | | 0.2 | 0.2 | 0.2 | | 0.2 | 0.2 | 0.2 | | | 0.2 | | | | |
| TSPP | | | | | | | | | 13.2 | 6.0 | 4.0 | 26.6 | | | |
| Silica | | | | 5.0 | 10.0 | | | | 4.0 | | | 4.0 | 4.0 | 10.0 | |
| Calcium Peroxide | | | | | 5.0 | | | | | | | | | | |
| Chlorhexidine digluconate | | | | 4.4 | | | | | | 3.2 | | | | | |
| Poloxamer 407 | 53.0 | 35.0 | | 20.0 | | | | 44.4 | | | 61.2 | 45.0 | 19.4 | | |
| PEG 8000 | | | | | | | | | | 11.7 | | | 33.0 | | |
| PEG 1450 | 35.0 | 53.0 | 71.1 | | | | | | 7.6 | | 10.0 | 8.0 | 33.0 | | |
| Sodium fluoride | | 0.1 | 0.1 | | | | | | | | | | 0.2 | | |
| Carrageenin | | | | | | | | 13.3 | | | | | | | |
| Silicone (PDMS) | | | | | | | | 17.6 | | | 10.0 | | | | |
| SnF$_2$ | | | | | | | | | | | | | | | 4.8 |

EXAMPLE 40

A saliva soluble base coating for multifilament dental floss was prepared having the following formula:

| Ingredient | Grams |
|---|---|
| Pluronic F-127 | 530 |
| PEG 1450 | 350 |
| PG | 1 |
| Insoluble saccharin | 23 |
| Peppermint flavor | 76 |
| L-menthol | 20 |
| Total | 1000 |

The foregoing was added to multifilament dental floss at various rates indicated in Table 5 below. This coated multifilament was overcoated with various particulate abrasives at various rates also, as indicated in Table 5 below.

TABLE 5

Coated Multifilament Dental Floss, Particulate Abrasive Overcoating Data

| | Multifilament Dental Floss | | Base Coating | | | Base Coat & Particulate | | Particulate | | |
|---|---|---|---|---|---|---|---|---|---|---|
| Ex No. | Multifilament Dental Floss Type (flavor) | Denier (grams/yd) | Base Coat Formula | Base Coat Load (mg/yd) | Particulate Type | Particulate Load (mg/yd) | Abrasive Load (mg/yd) | Particulate Abrasive % of total load | Abrasive % of Total Device | PAF |
| 41 | Polypropylene | 0.071 | Ex 40 | 0.0436 | Fine DCP | 0.0672 | 0.0236 | 35.1 | 17.1 | 1 |
| 42 | Polypropylene | 0.071 | Ex 40 | 0.0436 | Granular DCP | 0.0616 | 0.008 | 15.5 | 6.5 | 2 |
| 43 | Polypropylene | 0.071 | Ex 40 | 0.0436 | Silica | 0.0488 | 0.0052 | 10.7 | 4.3 | 2 |
| 44 | Polypropylene | 0.071 | Ex 40 | 0.04 | Pumice | 0.056 | 0.016 | 28.6 | 12.6 | 3 |
| 45 | Nylon | 0.09 | Ex 40 | 0.0332 | Granular DCP | 0.0416 | 0.0084 | 20.2 | 6.4 | 2 |
| 46 | Nylon | 0.09 | Ex 40 | 0.0332 | fine DCP | 0.0504 | 0.0172 | 34.1 | 12.3 | 1 |
| 47 | Texturized Multifilament J&J REACH® Gentle Gum Care | 0.082 | See U.S. Pat. No. 5,711,935 | 0.092 | Pumice | 0.107 | 0.015 | 14.0 | 79 | 2 |
| 48 | Texturized Multifilament J&J REACH® Gentle Gum Care (Spicemint) | 0.082 | See U.S. Pat. No. 5,711,935 | 0.089 | Pumice | 0.102 | 0.013 | 12.7 | 7.1 | 2 |
| 49 | Texturized Multifilament J&J REACH® Gentle Gum Care (Tartar Control) | 0.0822 | See U.S. Pat. No. 5,711,935 | 0.116 | Pumice | 0.1174 | 0.0014 | 1.2 | 0.7 | 1 |
| 50 | J&J (Waxed Mint) | 0.066 | Wax | 0.0864 | Silica | 0.1046 | 0.0184 | 17.6 | 21.3 | 2 |
| 51 | Ranir (Waxed Mint) | 0.085 | Wax | 0.0876 | Pumice Granular DCP | 0.0916 | 0.004 | 4.4 | 4.6 | 2 |
| 52 | Ranir Hi-Tech | 0.0686 | Wax | 0.1216 | Pumice | 0.1392 | 0.0176 | 12.6 | 14.5 | 3 |
| 53 | J&J Whitening Tape | 0.0667 | Wax | 0.0427 | — | — | — | — | — | — |

In one preferred embodiment of the invention, commercial versions of "waxed multifilament dental flosses" including J&J waxed flavored multifilament dental flosses, and a private label alternative thereof; can be improved dramatically by rendering the insoluble wax coatings on these multifilament flosses receptive to particulate abrasive impingement so that particulate abrasives become imbedded in the various wax coatings. These are described in detail in Examples 41 to 53 in Table 5.

Comparing the particulate abrasive overcoated versions of these wax coated multifilament dental flosses with the corresponding commercial waxed flosses that have not been overcoated with particulate abrasive, indicates a dramatic improvement in the "hand" of the particulate overcoating floss, as well as in the perception that the particulate abrasive overcoated floss is "working" indicated by the PAF values. These improvements are considered substantial and relevant and contribute to an overall enhanced perceived value of these particulate abrasive overcoated wax flosses. Compared to the commercial waxed flosses without these overcoatings.

In a second preferred embodiment of the invention, commercial versions of coated, texturized, multifilament dental floss, such as the various flavored versions of J&J's REACH® Gentle Gum Care, can be improved dramatically by rendering the saliva soluble "load" on the outside of these texturized multifilament flosses, receptive to particulate abrasive impingement so that particulate abrasives become imbedded in the saliva soluble coatings. These are described in detail in Examples 47 to 49 in Table 5.

Comparing the particulate abrasive overcoated versions of these coated, texturized, multifilament dental flosses, as described in Examples 47 to 49, with the corresponding coated, texturized, multifilament flosses without the particulate abrasive overcoating indicates a dramatic improvement in the "hand" of the particulate abrasive overcoated version, as well as in the perception that the particulate abrasive overcoated, texturized, multifilament dental floss is "working". See PAF values. These improvements are considered substantial and relevant and contribute to the overall enhanced perceived value of these particulate abrasive overcoated versions of texturized multifilament dental flosses, compared to the commercial versions without these overcoatings.

In a third preferred embodiment of the invention commercial versions of a coated multifilament dental flosses marketed as Hi-Tech™ Dental Floss by Ranir can be improved dramatically by rendering the coatings thereon receptive to particulate abrasive impingement so that particulate abrasives become imbedded in the coatings on this commercial product. See Example 52 in Table 5.

Comparing the particulate abrasive overcoated version coated Hi-Tech multifilament dental floss of Example 52 with the corresponding coated floss that has not been overcoated with particulate abrasive, indicates a dramatic improvement in the "hand" of the particulate abrasive overcoated Hi-Tech floss, as well as in this perception that the particulate abrasive overcoated Hi-Tech floss is "working". See PAF values. This improvement is considered substantial and relevant and contributes to an overall enhanced perceived value of the particulate abrasive overcoated Hi-Tech floss.

Comparing particulate abrasive overcoated versions of J&J's REACH® Gentle Gum Care and J&J Waxed Mint multifilament dental flosses (as described in Examples 47 to 50 in Table 5) with J&J Whitening Dental Tape (see Ex. 53), indicates the particulate abrasive overcoated versions of these two commercial multifilament dental flosses are preferred over J&J Whitening Dental Floss. This preference is in part attributed to the ease of use and ease of insertion indicated for the particulate abrasive overcoated multifilament dental flosses along with the perception that these particulate abrasive overcoated versions are "working" as further indicated by the PAF values.

A particularly preferred embodiment of the present invention is the enhanced perceived value imparted to a wide range of commercial waxed and/or coated multifilament dental flosses with very modest increases in cost-of-goods. This enhanced perceived value can be achieved by the addition of a modest priced particulate abrasive overcoating using an overcoating operation that can be installed in-line with current waxing and/or coating operations.

Commercial, coated, multifilament dental flosses such as described in Examples 41 through 53 in Table 5 can be further improved beyond the "it's working" perception, which is indicated by recorded PAF values. That is, a second overcoating with a saliva soluble particulate containing flavor, mouth feel agents, etc., can be imbedded into the wax base coating using a second separate fluidized bed and nozzle means to imbed this particulate into the liquid base coating before the multifilament floss enters the coating zone.

TABLE 6

Coated Multifilament Dental Floss Overcoated with Particulate Abrasive and Saliva Soluble Particulate

| | | | OVERCOATINGS | | | |
|---|---|---|---|---|---|---|
| Ex. No. | Multifilament Dental Floss & Denier (grams/yd) | Base Coating Type & Load (mg/yd) | Particulate Abrasive Type & Load (in mg/yd) | Projected PAF | Projected IRF | Saliva Soluble Particulate Type & Load (in mg/yd) | Projected Impact of Saliva Soluble Particulate |
| 54 | nylon 6,6 840 0.085 | microcrystalline wax (33) | pumice (21) | 3.4 | 96 | PEG 3350/flavor (14) | 3 X over wax flavor |
| 55 | nylon 6,6 840 0.085 | microcrystalline wax (33) | pumice (14) | 3.2 | 98 | PEG 3350/flavor (18) | 4 X over wax flavor |
| 56 | nylon 6,6 840 0.085 | microcrystalline wax (33) | silica (16) | 2.8 | 97 | PEG 3350/flavor (12) | 2 X over wax flavor |
| 57 | nylon 6,6 840 0.085 | bees wax (27) | pumice (22) | 3.5 | 92 | PEG 3350/flavor (14) | 2 X over wax flavor |
| 58 | nylon 6,6 840 0.085 | bees wax (27) | pumice (14) | 3.0 | 96 | PEG 3350/flavor (17) | 3 X over wax flavor |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Coated multifilament dental floss having a denier between about 300 and about 1000, said floss having two distinct coatings, including:
   (a) from between about 10 and about 100 mg/yd of base coating selected from the group consisting of saliva soluble coatings and saliva insoluble coatings, and
   (b) further including a biofilm-responsive particulate abrasive overcoating thereon and at least partially imbedded in the base coating,
   wherein said particulate abrasive overcoating comprises from between about 2 and about 45 percent by weight of said device; and
   whererin from between about 20 to about 90% of the total surface of each particulate in the overcoating is imbedded into the base coating on the multifilaments.

2. A coated multifilament dental device according to claim 1, wherein said imbedded biofilm-responsive particulate abrasive overcoating has an average particle size from between about 7 and 200 microns.

3. A coated multifilament dental device according to claim 1, wherein said imbedded biofilm-responsive particulate abrasive overcoating has a particle size distribution from between about 5 and about 300 microns.

4. Coated multifilament dental devices according to claim 1, wherein said overcoating also contains additional solid particulates selected from the group consisting of water soluble waxes, water soluble nonionic surfactants, an emulsion of polydimethyl siloxane and polyoxypropylene-polyoxyethylene block copolymers, a high shear mixture of high molecular weight block copolymers of ethylene oxide and propylene oxide with high viscosity polydimethylsiloxane polymers and mixtures thereof.

5. Coated multifilament dental devices according to claim 1, wherein said multifilament dental floss is selected from the group consisting of texturized, untwisted, tacked, twisted multifilaments and mixtures thereof.

6. Coated multifilament dental devices according to claim 1, wherein said coating contains a releasable antimicrobial.

7. Coated multifilament dental devices according to claim 1, wherein said biofilm-responsive particulate abrasive overcoating is a dental abrasive selected from the group consisting of silica, pumice, alumina, calcium carbonate, dicalcium phosphate dihydrate and mixtures thereof.

8. Coated multifilament dental devices according to claim 1, wherein said biofilm-responsive particulate abrasive overcoating is an active abrasive selected from the group consisting of whitening, tartar control, stain fighting, hypersensitivity treatment abrasives and mixtures thereof.

9. Coated multifilament dental devices according to claim 7, wherein said multifilament dental devices contains from between 2 and 12 multifilament bundles.

10. A coated multifilament device according to claim 1, wherein said multifilament construction is selected from the strand types consisting of: 140 denier and 68 filaments, 100 denier and 34 filaments, 70 denier and 34 filaments, and combinations thereof.

11. A coated multifilament dental device according to claim 1, wherein said base coating is saliva insoluble and said biofilm responsive particulate abrasive overcoating is insoluble.

* * * * *